US010070905B2

(12) United States Patent
Bottlang et al.

(10) Patent No.: US 10,070,905 B2
(45) Date of Patent: *Sep. 11, 2018

(54) FLEXIBLE PLATE FIXATION OF BONE FRACTURES

(71) Applicant: Zimmer, Inc., Warsaw, IN (US)

(72) Inventors: Michael Bottlang, Happy Valley, OR (US); Steven M. Madey, West Linn, OR (US); Kyle Wirtz, Portland, OR (US); Stanley Tsai, Portland, OR (US)

(73) Assignee: Zimmer, Inc., Warsaw, IN (US)

( * ) Notice: Subject to any disclaimer, the term of this patent is extended or adjusted under 35 U.S.C. 154(b) by 406 days.

This patent is subject to a terminal disclaimer.

(21) Appl. No.: 14/808,773

(22) Filed: Jul. 24, 2015

(65) Prior Publication Data

US 2015/0327896 A1 Nov. 19, 2015

Related U.S. Application Data

(63) Continuation-in-part of application No. 13/755,493, filed on Jan. 31, 2013, now Pat. No. 9,295,508.
(Continued)

(51) Int. Cl.
*A61B 17/56* (2006.01)
*A61B 17/58* (2006.01)
(Continued)

(52) U.S. Cl.
CPC .......... *A61B 17/8047* (2013.01); *A61B 17/86* (2013.01); *A61B 17/8057* (2013.01);
(Continued)

(58) Field of Classification Search
CPC . A61B 17/80; A61B 17/8004; A61B 17/8033; A61B 17/8047; A61B 17/8052; A61B 17/8057; A61B 17/8061
(Continued)

(56) References Cited

U.S. PATENT DOCUMENTS 2,406,832 A 9/1946 Hardinge
2,580,821 A 1/1952 Toufick
(Continued)

FOREIGN PATENT DOCUMENTS

CN 104135953 A 11/2014
CN 106794036 5/2017
(Continued)

OTHER PUBLICATIONS

"U.S. Appl. No. 13/166,539, Final Office Action dated May 21, 2014", 9 pgs.
(Continued)

*Primary Examiner* — Si Ming Ku
(74) *Attorney, Agent, or Firm* — Schwegman Lundberg & Woessner, P.A.

(57) ABSTRACT

A device can be provided that includes a bone plate having an upper surface and a bone-facing surface, wherein the bone plate includes one or more openings extending through the bone plate from the upper surface to the bone-facing surface, and one or more sliding elements each including a fastener receiving hole. The one or more openings can at least partially surround a periphery of one of the receiving holes. Further, the one or more openings can be at least partially filled with an elastomer to support elastic suspension of the one or more sliding elements in the bone plate, thereby enabling relative displacement between the one or more sliding elements and the bone plate. At least one sensor can also be provided that is operable to assess a dynamic parameter of one of the one or more sliding elements within the bone plate.

20 Claims, 19 Drawing Sheets

Related U.S. Application Data

(60) Provisional application No. 61/594,560, filed on Feb. 3, 2012, provisional application No. 62/029,168, filed on Jul. 25, 2014.

(51) Int. Cl.
  *A61B 17/80* (2006.01)
  *A61F 2/30* (2006.01)
  *A61B 17/86* (2006.01)
  *A61B 17/00* (2006.01)

(52) U.S. Cl.
  CPC ........... *A61B 2017/00221* (2013.01); *A61B 2017/00862* (2013.01); *A61B 2560/0219* (2013.01); *A61B 2562/0219* (2013.01)

(58) Field of Classification Search
  USPC ................................. 606/280–299, 70, 71
  See application file for complete search history.

(56) References Cited

U.S. PATENT DOCUMENTS

| | | | |
|---|---|---|---|
| 3,807,394 A | 4/1974 | Attenborough | |
| 4,029,091 A | 6/1977 | Von Bezold et al. | |
| 4,338,296 A | 7/1982 | Lobmann et al. | |
| 4,361,153 A | 11/1982 | Slocum et al. | |
| 4,743,260 A | 5/1988 | Burton | |
| 4,905,679 A | 3/1990 | Morgan | |
| 4,943,292 A | 7/1990 | Foux | |
| 5,306,310 A | 4/1994 | Siebels | |
| 5,423,816 A | 6/1995 | Lin | |
| 5,468,242 A | 11/1995 | Reisberg | |
| 5,578,034 A | 11/1996 | Estes | |
| 5,578,036 A | 11/1996 | Stone et al. | |
| 5,681,311 A | 10/1997 | Foley et al. | |
| 5,709,686 A | 1/1998 | Talos et al. | |
| 5,741,258 A | 4/1998 | Klaue et al. | |
| 5,743,913 A | 4/1998 | Wellisz | |
| 5,984,925 A | 11/1999 | Apgar | |
| 6,093,188 A | 4/2000 | Apgar | |
| 6,206,882 B1 | 3/2001 | Cohen | |
| 6,340,632 B1 | 1/2002 | Fukada et al. | |
| 6,364,881 B1 | 4/2002 | Apgar et al. | |
| 6,540,746 B1 | 4/2003 | Buhler et al. | |
| 6,663,632 B1 | 12/2003 | Frigg | |
| 6,755,832 B2 | 6/2004 | Happomem et al. | |
| 6,986,771 B2 | 1/2006 | Paul et al. | |
| 6,989,011 B2 | 1/2006 | Paul et al. | |
| 7,048,739 B2 | 5/2006 | Konieczynski et al. | |
| 7,175,624 B2 | 2/2007 | Konieczynski et al. | |
| 7,189,237 B2 | 3/2007 | Huebner | |
| 7,276,070 B2 | 10/2007 | Mückter | |
| 7,341,591 B2 | 3/2008 | Grinberg | |
| 7,377,921 B2 | 5/2008 | Studer et al. | |
| 7,452,370 B2 | 11/2008 | Anderson | |
| 7,572,282 B2 | 8/2009 | Boomer et al. | |
| 7,591,840 B2 | 9/2009 | Suddaby | |
| D603,503 S | 11/2009 | Kriska et al. | |
| D603,504 S | 11/2009 | Kriska et al. | |
| D603,505 S | 11/2009 | Kriska et al. | |
| D603,507 S | 11/2009 | Kriska et al. | |
| D603,508 S | 11/2009 | Kriska et al. | |
| D603,510 S | 11/2009 | Kriska et al. | |
| D603,511 S | 11/2009 | Kriska et al. | |
| D603,961 S | 11/2009 | Kriska et al. | |
| D603,962 S | 11/2009 | Kriska et al. | |
| D603,963 S | 11/2009 | Kriska et al. | |
| D603,964 S | 11/2009 | Kriska et al. | |
| 7,621,942 B2 | 11/2009 | Piehl | |
| 7,641,675 B2 | 1/2010 | Lindemann et al. | |
| 7,651,517 B2 | 1/2010 | Konieczynski et al. | |
| 7,749,257 B2 | 7/2010 | Medoff | |
| 7,806,914 B2 | 10/2010 | Boyd et al. | |
| 7,811,312 B2 | 10/2010 | Stevens et al. | |
| 7,833,256 B2 | 11/2010 | Biedermann et al. | |
| 7,842,037 B2 | 11/2010 | Schulze | |
| 7,887,569 B2 | 2/2011 | Frigg | |
| 7,887,587 B2 | 2/2011 | Griffiths et al. | |
| 7,914,561 B2 | 3/2011 | Konieczynski et al. | |
| 8,486,070 B2 | 7/2013 | Morgan et al. | |
| 8,687,865 B2 | 4/2014 | Wilson et al. | |
| 8,790,379 B2 | 7/2014 | Madey et al. | |
| 8,882,815 B2 | 11/2014 | Bottlang et al. | |
| 8,992,583 B2 | 3/2015 | Bottlang et al. | |
| 9,101,423 B2 | 8/2015 | Hulliger | |
| 9,295,508 B2 | 3/2016 | Bottlang et al. | |
| 9,510,879 B2 | 12/2016 | Bottlang et al. | |
| 9,700,361 B2 | 7/2017 | Bottlang et al. | |
| 9,763,713 B2 | 9/2017 | Bottlang et al. | |
| 9,788,873 B2 | 10/2017 | Bottlang et al. | |
| 2002/0150671 A1 | 10/2002 | Koulik et al. | |
| 2004/0006343 A1 | 1/2004 | Sevrain | |
| 2004/0019353 A1 | 1/2004 | Freid et al. | |
| 2004/0097937 A1 | 5/2004 | Pike et al. | |
| 2004/0193155 A1 | 9/2004 | Castaneda | |
| 2004/0220570 A1 | 11/2004 | Frigg | |
| 2005/0090825 A1 | 4/2005 | Pfefferle et al. | |
| 2005/0096657 A1 | 5/2005 | Autericque et al. | |
| 2005/0116930 A1 | 6/2005 | Gates | |
| 2005/0196421 A1 | 9/2005 | Hunter et al. | |
| 2005/0216008 A1 | 9/2005 | Zwirnmann et al. | |
| 2005/0273105 A1 | 12/2005 | Konieczynski et al. | |
| 2005/0288668 A1 | 12/2005 | Brinkhaus | |
| 2006/0058796 A1 | 3/2006 | Hartdegen et al. | |
| 2006/0116682 A1 | 6/2006 | Longo | |
| 2006/0155282 A1 | 7/2006 | Vese | |
| 2006/0195099 A1 | 8/2006 | Bottlang | |
| 2006/0241612 A1 | 10/2006 | Medoff | |
| 2006/0247638 A1 | 11/2006 | Trieu et al. | |
| 2006/0247639 A1 | 11/2006 | Anderson | |
| 2006/0264949 A1 | 11/2006 | Kohut et al. | |
| 2007/0055251 A1* | 3/2007 | Huebner | A61B 17/8047 606/279 |
| 2007/0118127 A1 | 5/2007 | Serhan et al. | |
| 2007/0213729 A1 | 9/2007 | Lindemann et al. | |
| 2008/0027439 A1 | 1/2008 | Sasing | |
| 2008/0083613 A1 | 4/2008 | Oi et al. | |
| 2008/0097445 A1* | 4/2008 | Weinstein | A61B 17/8023 606/281 |
| 2008/0147122 A1 | 6/2008 | Jackson | |
| 2008/0147125 A1 | 6/2008 | Colleran et al. | |
| 2008/0200955 A1 | 8/2008 | Tepic | |
| 2008/0275509 A1 | 11/2008 | Clifford et al. | |
| 2008/0306536 A1 | 12/2008 | Frigg et al. | |
| 2009/0012571 A1* | 1/2009 | Perrow | A61B 17/1671 606/280 |
| 2009/0030467 A1 | 1/2009 | Sonohata et al. | |
| 2009/0036930 A1 | 2/2009 | Allison | |
| 2009/0043341 A1 | 2/2009 | Tyber et al. | |
| 2009/0062915 A1 | 3/2009 | Kohm et al. | |
| 2009/0118768 A1 | 5/2009 | Sixto, Jr. et al. | |
| 2009/0118769 A1 | 5/2009 | Sixto, Jr. et al. | |
| 2009/0118770 A1 | 5/2009 | Sixto, Jr. et al. | |
| 2009/0125067 A1 | 5/2009 | Mazzuca et al. | |
| 2009/0125069 A1 | 5/2009 | Sixto, Jr. et al. | |
| 2009/0125070 A1 | 5/2009 | Sixto, Jr. et al. | |
| 2009/0157121 A1 | 6/2009 | Harris et al. | |
| 2009/0157123 A1 | 6/2009 | Appenzeller et al. | |
| 2009/0222049 A1 | 9/2009 | Frigg et al. | |
| 2009/0234393 A1 | 9/2009 | Sournac et al. | |
| 2009/0270924 A1 | 10/2009 | Wing et al. | |
| 2009/0318921 A1 | 12/2009 | White et al. | |
| 2009/0318976 A1 | 12/2009 | Gabriel et al. | |
| 2010/0010541 A1 | 1/2010 | Boomer et al. | |
| 2010/0036430 A1 | 2/2010 | Hartdegen et al. | |
| 2010/0076495 A1 | 3/2010 | Lindemann et al. | |
| 2010/0094351 A1 | 4/2010 | Haggenmaker et al. | |
| 2010/0114177 A1 | 5/2010 | Piehl | |
| 2010/0131012 A1 | 5/2010 | Ralph et al. | |
| 2010/0131013 A1 | 5/2010 | Ralph et al. | |
| 2010/0217327 A1 | 8/2010 | Vancelette et al. | |
| 2010/0249850 A1 | 9/2010 | Cerynik et al. | |
| 2010/0305569 A1 | 12/2010 | Leuenberger et al. | |

(56) References Cited

U.S. PATENT DOCUMENTS

| | | | |
|---|---|---|---|
| 2011/0029024 | A1 | 2/2011 | Crainich |
| 2011/0118742 | A1 | 5/2011 | Hulliger et al. |
| 2011/0319942 | A1 | 12/2011 | Bottlang et al. |
| 2012/0143193 | A1 | 6/2012 | Hulliger |
| 2012/0277746 | A1 | 11/2012 | Morgan et al. |
| 2012/0310289 | A1 | 12/2012 | Bottland et al. |
| 2013/0006310 | A1 | 1/2013 | Bottlang et al. |
| 2013/0204304 | A1 | 8/2013 | Bottlang et al. |
| 2014/0330275 | A1 | 11/2014 | Bottlang et al. |
| 2015/0025588 | A1 | 1/2015 | Bottlang et al. |
| 2015/0230840 | A1 | 8/2015 | Bottlang et al. |
| 2016/0074082 | A1* | 3/2016 | Cremer ............. A61B 17/8085 606/70 |
| 2016/0081729 | A1 | 3/2016 | Velikov et al. |
| 2016/0157905 | A1 | 6/2016 | Arellano et al. |
| 2016/0166293 | A1 | 6/2016 | Bottlang et al. |
| 2017/0273728 | A1 | 9/2017 | Bottlang et al. |
| 2018/0036048 | A1 | 2/2018 | Bottlang et al. |
| 2018/0070997 | A1 | 3/2018 | Bottlang et al. |

FOREIGN PATENT DOCUMENTS

| | | |
|---|---|---|
| CN | 108186101 A | 6/2018 |
| EP | 0615728 A2 | 9/1994 |
| EP | 1926445 A1 | 6/2008 |
| EP | 2005978 A1 | 12/2008 |
| FR | 742618 A | 1/1933 |
| FR | 2634368 A1 | 1/1990 |
| JP | 2005507953 A | 3/2005 |
| JP | 2009501575 A | 1/2009 |
| JP | 2009505751 A | 2/2009 |
| JP | 2010521274 A | 6/2010 |
| JP | 2015507953 A | 3/2015 |
| WO | WO-200506557 A1 | 7/2005 |
| WO | WO-2007009124 A2 | 1/2007 |
| WO | 2007056874 | 5/2007 |
| WO | WO-2009039430 A1 | 3/2009 |
| WO | WO-2010037984 A1 | 4/2010 |
| WO | WO-2010111350 A1 | 9/2010 |
| WO | WO-2010132252 A1 | 11/2010 |
| WO | WO-2011163387 A2 | 12/2011 |
| WO | WO-2013021357 A1 | 2/2013 |
| WO | 2013116642 A1 | 8/2013 |
| WO | WO-2016014977 A1 | 1/2016 |

OTHER PUBLICATIONS

"U.S. Appl. No. 13/166,539, Non Final Office Action dated Jan. 2, 2014", 10 pgs.
"U.S. Appl. No. 13/166,539, Non Final Office Action dated Jun. 28, 2013", 10 pgs.
"U.S. Appl. No. 13/166,539, Notice of Allowability dated Oct. 9, 2014", 4 pgs.
"U.S. Appl. No. 13/166,539, Notice of Allowance dated Aug. 15, 2014", 7 pgs.
"U.S. Appl. No. 13/166,539, Preliminary Amendment filed Jul. 19, 2012", 7 pgs.
"U.S. Appl. No. 13/166,539, Response filed Jan. 28, 2014 to Non Final Office Action dated Jan. 2, 2014", 3 pgs.
"U.S. Appl. No. 13/166,539, Response filed May 2, 2014 to Non Final Office Action dated Jan. 2, 2014", 14 pgs.
"U.S. Appl. No. 13/166,539, Response filed May 6, 2013 to Restriction Requirement dated Mar. 5, 2013", 9 pgs.
"U.S. Appl. No. 13/166,539, Response filed Jul. 21, 2014 to Final Office Action dated May 21, 2014", 13 pgs.
"U.S. Appl. No. 13/166,539, Response filed Oct. 28, 2013 to Non Final Office Action dated Jun. 28, 2013", 10 pgs.
"U.S. Appl. No. 13/166,539, Restriction Requirement dated Mar. 5, 2013", 6 pgs.
"U.S. Appl. No. 13/490,249, Amendment filed Jan. 28, 2014", 3 pgs.
"U.S. Appl. No. 13/490,249, Non Final Office Action dated Sep. 19, 2013", 10 pgs.
"U.S. Appl. No. 13/490,249, Notice of Allowance dated Mar. 27, 2014", 7 pgs.
"U.S. Appl. No. 13/490,249, Response filed Jan. 21, 2014 to Non Final Office Action dated Sep. 19, 2013", 12 pgs.
"U.S. Appl. No. 13/490,249, Response filed May 7, 2013 to Restriction Requirement dated Mar. 7, 2013", 11 pgs.
"U.S. Appl. No. 13/490,249, Response filed to Restriction Requirement dated Jul. 2, 2013", 6 pgs.
"U.S. Appl. No. 13/490,249, Restriction Requirement dated Mar. 7, 2013", 7 pgs.
"U.S. Appl. No. 13/490,249, Restriction Requirement dated Jul. 2, 2013", 8 pgs.
"U.S. Appl. No. 13/554,119, Advisory Action dated Feb. 12, 2014", 2 pgs.
"U.S. Appl. No. 13/554,119, Final Office Action dated Sep. 19, 2013", 9 pgs.
"U.S. Appl. No. 13/554,119, Non Final Office Action dated Mar. 13, 2013", 6 pgs.
"U.S. Appl. No. 13/554,119, Non Final Office Action dated Jul. 16, 2014", 7 pgs.
"U.S. Appl. No. 13/554,119, Notice of Allowance dated Nov. 24, 2014", 5 pgs.
"U.S. Appl. No. 13/554,119, Preliminary Amendment filed Jun. 20, 2012", 5 pgs.
"U.S. Appl. No. 13/554,119, Response filed Jan. 28, 2014 to Final Office Action dated Sep. 19, 2013", 3 pgs.
"U.S. Appl. No. 13/554,119, Response filed Mar. 19, 2014 to Advisory Action dated Feb. 12, 2014", 13 pgs.
"U.S. Appl. No. 13/554,119, Response filed Aug. 13, 2013 to Non Final Office Action dated Mar. 13, 2013", 8 pgs.
"U.S. Appl. No. 13/554,119, Response filed Oct. 16, 2014 to Non Final Office Action dated Jul. 16, 2014", 12 pgs.
"U.S. Appl. No. 13/755,493, Advisory Action dated Dec. 4, 2015", 4 pgs.
"U.S. Appl. No. 13/755,493, Examiner Interview Summary dated Dec. 4, 2015", 1 pg.
"U.S. Appl. No. 13/755,493, Final Office Action dated Jul. 9, 2015", 12 pgs.
"U.S. Appl. No. 13/755,493, Non Final Office Action dated Nov. 19, 2014", 13 pgs.
"U.S. Appl. No. 13/755,493, Preliminary Amendment dated Jan. 28, 2014", 3 pgs.
"U.S. Appl. No. 13/755,493, Response filed Feb. 19, 2015 to Non-Final Office Action dated Nov. 19, 2014", 16 pgs.
"U.S. Appl. No. 13/755,493, Response filed Oct. 28, 2014 to Restriction Requirement dated Oct. 9, 2014", 9 pgs.
"U.S. Appl. No. 13/755,493, Response filed Nov. 12, 2015 to Final Office Action dated Jul. 9, 2015", 15 pgs.
"U.S. Appl. No. 13/755,493, Restriction Requirement dated Oct. 9, 2014", 6 pgs.
"U.S. Appl. No. 13/755,493, Supplemental Preliminary Amendment dated Jan. 30, 2014", 3 pgs.
"U.S. Appl. No. 14/308,286, Preliminary Amendment filed Sep. 17, 2014", 7 pgs.
"U.S. Appl. No. 14/308,314, Preliminary Amendment filed Sep. 17, 2014", 7 pgs.
"U.S. Appl. No. 14/630,938, Preliminary Amendment filed Oct. 19, 2015", 7 pgs.
"Australian Application Serial No. 2011270934, First Examiner Report dated Sep. 12, 2013", 4 pgs.
"Australian Application Serial No. 2011270934, Response filed Jun. 30, 2014 to First Examiner Report dated Sep. 12, 2013", 20 pgs.
"Australian Application serial No. 2014265031, Non Final Office Action dated Sep. 21, 2015", 3 pgs.
"Australian Application Serial No. 2014265031, Preliminary Amendment filed Jul. 28, 2015", 13 pgs.
"European Application Serial No. 11798862.6, Extended European Search Report dated Mar. 16, 2015", 12 pgs.
"European Application Serial No. 11798862.6, Office Action dated Feb. 1, 2013", 2 pgs.
"European Application Serial No. 11798862.6, Response filed Jul. 30, 2013 to Office Action dated Feb. 1, 2013", 8 pgs.

(56) References Cited

OTHER PUBLICATIONS

"European Application Serial No. 13743819.8, Extended European Search Report dated Nov. 11, 2015", 9 pgs.
"European Application Serial No. 13743819.8, Preliminary Amendment filed Mar. 26, 2015", 11 pgs.
"International Application Serial No. PCT/US2011/041484, International Preliminary Report on Patentability dated Jan. 10, 2013", 6 pgs.
"International Application Serial No. PCT/US2011/041484, International Search Report dated Feb. 17, 2012", 4 pgs.
"International Application Serial No. PCT/US2013/024336, International Preliminary Report on Patentability dated Aug. 14, 2014", 10 pgs.
"International Application Serial No. PCT/US2013/024336, International Search Report dated May 15, 2013", 4 pgs.
"International Application Serial No. PCT/US2013/024336, Written Opinion dated May 15, 2013", 8 pgs.
"International Application Serial No. PCT/US2015/042057, International Search Report dated Oct. 16, 2015", 4 pgs.
"International Application Serial No. PCT/US2015/042057, Written Opinion dated Oct. 16, 2015", 6 pgs.
Bottlang, et al., "A Nonlocking End Screw Can Decrease Fracture Risk Caused by Locked Plating in the Osteoporotic Diaphysis", Journal of Bone & Joint Surgery, vol. 91, (2009), 620-627 pgs.
Bottlang, et al., "Effects of Construct Stiffness on Healing of Fractures Stabilzed with Locking Plates", Journal of Bone & Joint Surgery, vol. 92, (2010), 12-22 pgs.
Fitzpatrick, Dan C, et al., "Relative Stability of Conventional and Locked Plating Fixation in a Model of the Osteoporotic Femoral Diaphysis", Journal of Clinical Biomechanics 24(2), (Feb. 2009), 203-209.
Gard, S. A, et al., "The effect of a shock-absorbing pylon on the gait of persons with unilateral transtibial amputation.", Journal of Rehabilitation Research and Development 40(2), (2003), 109-124.
"U.S. Appl. No. 14/308,286, Corrected Notice of Allowance dated Jun. 28, 2016", 4 pgs.
"U.S. Appl. No. 14/308,286, Notice of Allowance dated Aug. 5, 2016", 7 pgs.
"U.S. Appl. No. 14/308,314, Final Office Action dated Aug. 25, 2016", 8 pgs.
"U.S. Appl. No. 14/308,314, Non Final Office Action dated Feb. 7, 2017", 9 pgs.
"U.S. Appl. No. 14/308,314, Response filed Jul. 25, 2016 to Non Final Office Action dated Mar. 23, 2016", 11 pgs.
"U.S. Appl. No. 14/308,314, Response filed Nov. 23, 2016 to Final Office Action dated Aug. 25, 2016", 10 pgs.
"U.S. Appl. No. 14/630,938, Final Office Action dated Dec. 20, 2016", 5 pgs.
"U.S. Appl. No. 14/630,938, Non Final Office Action dated Aug. 9, 2016", 14 pgs.
"U.S. Appl. No. 14/630,938, Notice of Allowance dated Mar. 27, 2017", 5 pgs.
"U.S. Appl. No. 14/630,938, Response filed Feb. 28, 2017 to Final Office Action dated Dec. 20, 2016", 11 pgs.
"U.S. Appl. No. 14/630,938, Response filed Nov. 9, 2016 to Non Final Office Action dated Aug. 9, 2016", 16 pgs.
"U.S. Appl. No. 15/047,702, Notice of Allowance dated Feb. 7, 2017", 5 pgs.
"U.S. Appl. No. 15/047,702, Notice of Allowance dated Oct. 7, 2016", 5 pgs.
"U.S. Appl. No. 15/047,702, PTO Response to Rule 312 Communication dated Feb. 17, 2017", 2 pgs.
"Australian Application Serial No. 2013214894, Amendment filed Mar. 8, 2017", 2 pgs.
"Australian Application Serial No. 2013214894, First Examiner Report dated Oct. 6, 2016", 3 pgs.
"Australian Application Serial No. 2013214894, Response Filed Mar. 3, 2017 to Office Action dated Oct. 6, 2017", 17 pgs.
"Australian Application Serial No. 2016203422, First Examiners Report dated Oct. 19, 2016", 4 pgs.
"Australian Application Serial No. 2016203422, Response Filed Mar. 2, 2016 to Office Action dated Oct. 19, 2016", 9 pgs.
"Canadian Application Serial No. 2,803,585, Office Action dated Jan. 25, 2017", 4 pgs.
"Chinese Application Serial No. 201380011448.7, Office Action dated Oct. 27, 2016", (W/ English Translation), 19 pgs.
"Chinese Application Serial No. 201380011448.7, Response filed Jan. 11, 2017 to Office Action dated Oct. 27, 2016", (With English translation of claims), 10 pgs.
"Chinese Application Serial No. 201380011448.7, Response filed Jul. 8, 2016 to Office Action dated Dec. 25, 2015", 7 pgs.
"International Application Serial No. PCT/US2015/042057, International Preliminary Report on Patentability dated Feb. 9, 2017", 8 pgs.
"Japanese Application Serial No. 2014-555748, Office Action dated Nov. 15, 2016", (W/ English Translation), 6 pgs.
"Japanese Application Serial No. 2014-555748, Response Filed Feb. 15, 2017 to Office Action dated Nov. 15, 2016", (W/ English Translation), 14 pgs.
Rockwood, Charles A, et al., Rockwood and Green's fractures in adults, Lippincott Company, (Jan. 1, 1991), 16 pgs.
"U.S. Appl. No. 13/755,493, Notice of Allowance dated Dec. 23, 2015", 5 pgs.
"U.S. Appl. No. 13/755,493, Response filed Dec. 9, 2015 to Advisory Action dated Dec. 4, 2015", 12 pgs.
"U.S. Appl. No. 14/303,286, Notice of Allowance dated Mar. 23, 2016", 8 pgs.
"U.S. Appl. No. 14/308,314, Non Final Office Action dated Mar. 23, 2016", 9 pgs.
"Chinese Application Serial No. 201380011448.7, Office Action dated Dec. 25, 2015", (W/English Translation), 27 pgs.
"Standard specification for wrought titanium-6Aluminum-4Vanadium ELI (Extra Low Interstitial) alloy for surgical implant application. (UNS R56401)", ASTM F136-11, (2003), 5 pgs.
"Standard Test Methods for Equipment and Procedures Used in Evaluating the Performance Characteristics of Protective Headgear. Impact Test Apparatus.", ASMT F1446-13, (2013), 12 pgs.
Beaupre, G. S. et al., "A Comparison of Unicortical and Bicortical End Screw Attachment of Fracture Fixation Plates", Journal of Orthopaedic Trauma 6(3), (Feb. 1992), 294-300.
Davenport, Stephen R, et al., "Dynamic Compression Plate Fixation: A Biomechanical Comparison of Unicortical vs Bicortical Distal Screw Fixation", Journal of Orthopaedic Trauma 2(2), (Feb. 1988), 146-150.
Egol, Kenneth A, et al., "Biomechanics of Locked Plates and Screws", Journal of Orthopaedic Trauma 18(8), (Oct. 2004), 488-493.
Escott, Benjamin G, et al., "NeuFlex and Swanson Metacarpophalangeal Implants for Rheumatoid Arthritis: Prospective Randomized, Controlled Clinical Trial", The Journal of hand surgery 35(1), (Jan. 2010), 44-51.
Foliart, Donna E, "Synovitis and silicone joint implants: a summary of reported cases", Journal of Plastic and Reconstructive Surgery 99(1), (Jan. 1997), 245-252.
Gaggl, A, et al., "Biomechanical properties in titanium implants with integrated maintenance free shock absorbing elements", Journal of Biomaterials 22(2001), (Nov. 15, 2001), 3061-3066.
Gracis, S. E, et al., "Shock absorbing behavior of five restorative materials used on implants.", The International journal of prosthodontics 4(3), (Jan. 1992), 282-291.
"U.S. Appl. No. 14/308,314, Response filed May 8, 2017 to Non Final Office Action dated Feb. 7, 2017", 12 pgs.
"U.S. Appl. No. 14/630,938, Notice of Allowance dated May 19, 2017", 7 pgs.
"U.S. Appl. No. 15/047,702, Notice of Allowance dated May 25, 2017", 6 pgs.
"U.S. Appl. No. 14/308,314, Notice of Allowance dated Jun. 12, 2017", 5 pgs.
"European Application Serial No. 11798862.6, Communication Pursuant to Article 94(3) EPC dated May 19, 2017", 10 pgs.
"European Application Serial No. 11798862.6, Response filed Oct. 8, 2015 to Extended European Search Report dated Mar. 16, 2015", 9 pgs.

(56) References Cited

OTHER PUBLICATIONS

"Chinese Application Serial No. 201380011448.7, Office Action dated May 23, 2017", (W/ English Translation), 4 pgs.
"U.S. Appl. No. 15/616,608, Preliminary Amendment filed Jun. 23, 2017", 7 pgs.
"Chinese Application Serial No. 201380011448.7, Response filed Jul. 24, 2017 to Office Action dated May 23, 2017", w/ English Claims, 8 pgs.
"Canadian Application Serial No. 2,803,585, Response filed Jul. 5, 2017 to Office Action dated Jan. 25, 2017", 14 pgs.
"Japanese Application Serial No. 2014-555748, Examiners Decision of Final Refusal dated Aug. 8, 2017", (English Translation), 8 pgs.
"European Application Serial No. 15745735.9, Response filed Sep. 19, 2017 to Office Action dated Mar. 9, 2017", 13pgs.
"European Application Serial No. 13743819.8, Communication Pursuant to Article 94(3) EPC dated Sep. 20, 2017", 6 pgs.
"European Application Serial No. 11798862.6, Response filed Sep. 25, 2017 to Communication Pursuant to Article 94(3) EPC dated May 19, 2017", 15pgs.
"U.S. Appl. No. 15/616,608, Non Final Office Action dated Oct. 19, 2017", 5 pgs.
"U.S. Appl. No. 15/616,608, Response filed Jan. 19, 2018 to Non Final Office Action dated Oct. 19, 2017", 8 pgs.
"Canadian Application Serial No. 2,803,585, Office Action dated Oct. 23, 2017", 4 pgs.
"European Application Serial No. 13743819.8, Response filed Jan. 30, 2018 to Communication Pursuant to Article 94(3) EPC dated Sep. 20, 2017", 14 pgs.
"Japanese Application Serial No. 2014-555748, Response filed Dec. 17, 2017 to Examiners Decision of Final Refusal dated Aug. 8, 2017", w/ translation, 14 pgs.
"U.S. Appl. No. 15/712,967, Non Final Office Action dated Feb. 23, 2018", 5 pgs.
"U.S. Appl. No. 15/616,608, Corrected Notice of Allowance dated Mar. 28, 2018", 4 pgs.
"U.S. Appl. No. 15/616,608, Notice of Allowance dated Mar. 13, 2018", 5 pgs.
"Australian Application Serial No. 2015292319, Response filed Jul. 20, 2018 to First Examination Report dated May 17, 2018", 22 pgs.
"Japanese Application Serial No. 2017-504059, Notification of Reasons for Rejection dated Jun. 5, 2018", (W/ English Translation), 7 pgs.

\* cited by examiner

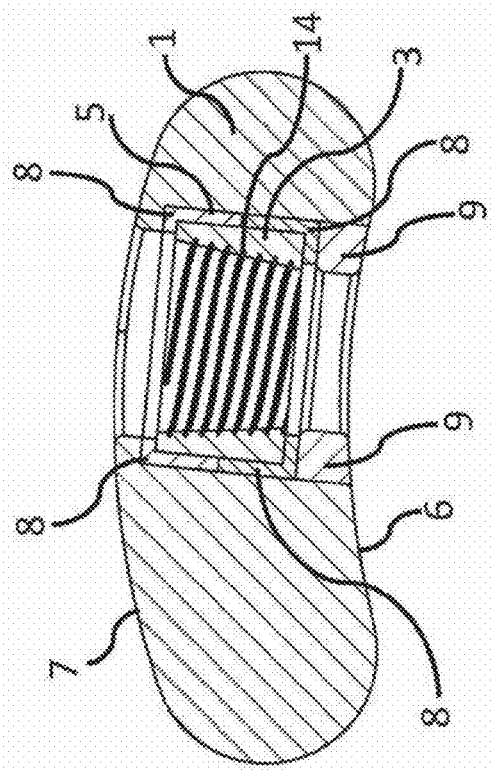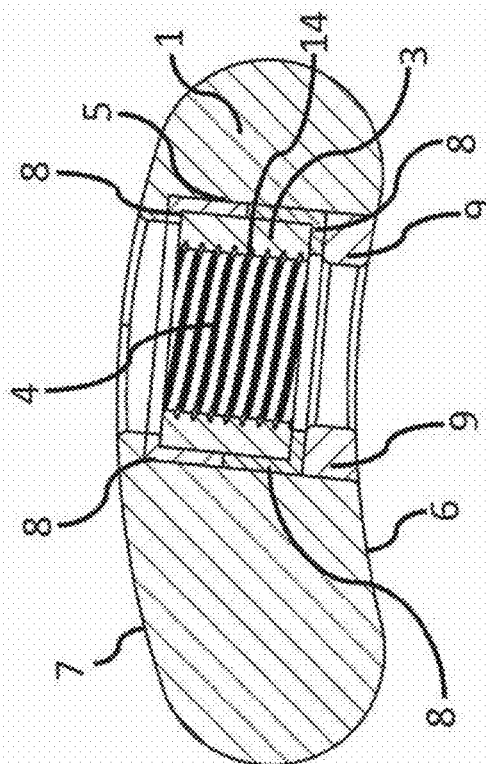

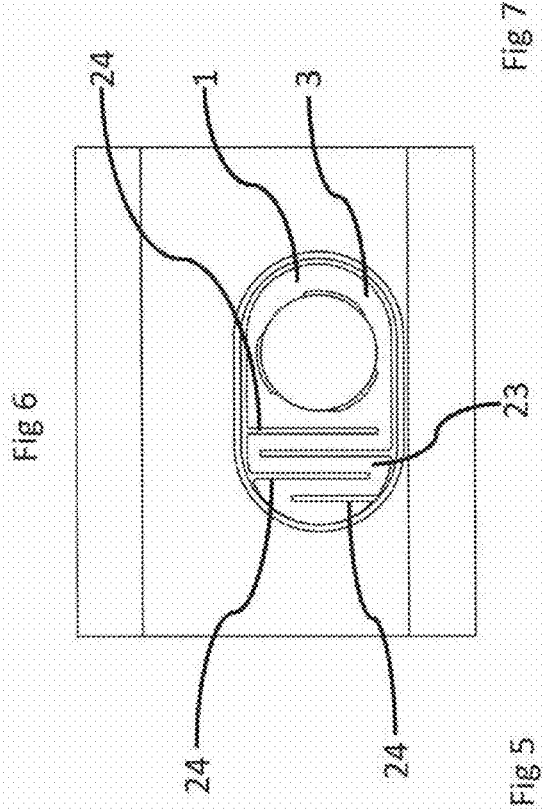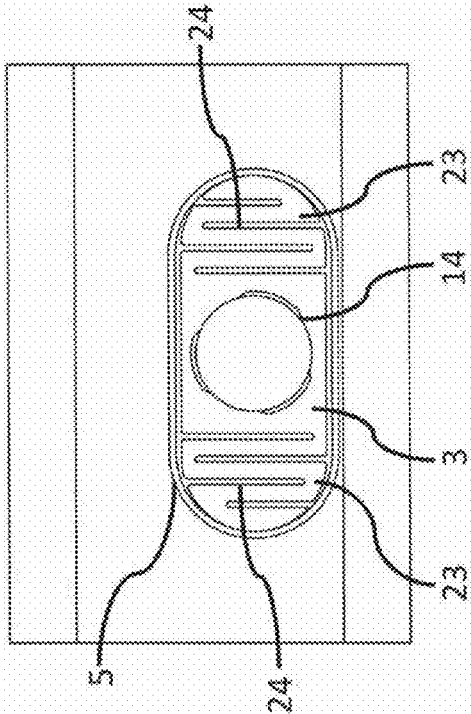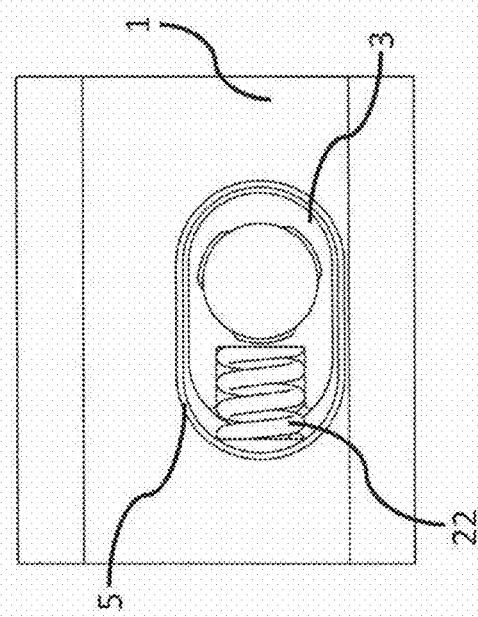

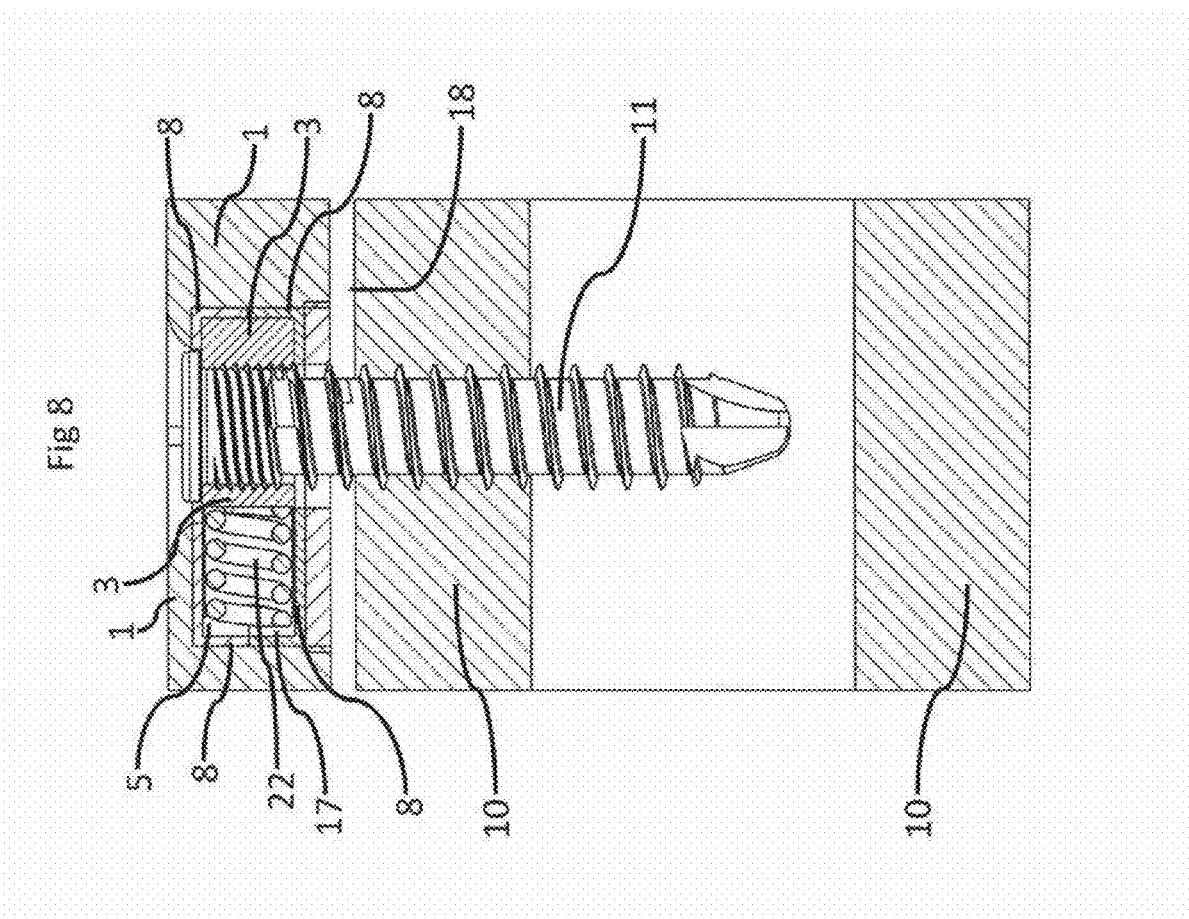

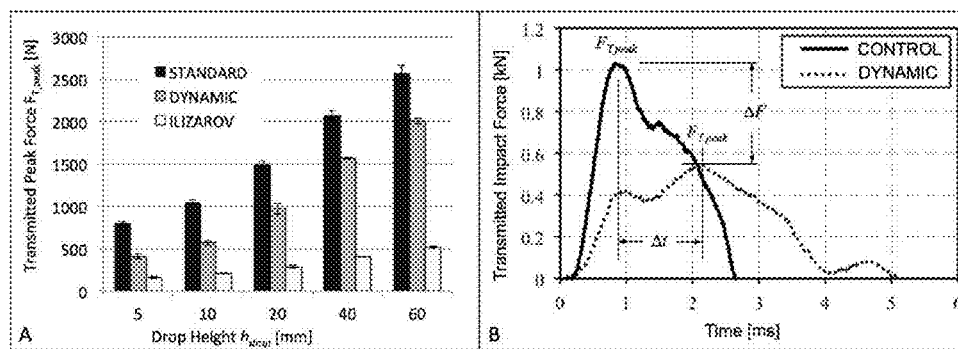
Fig. 20A                    Fig. 20B
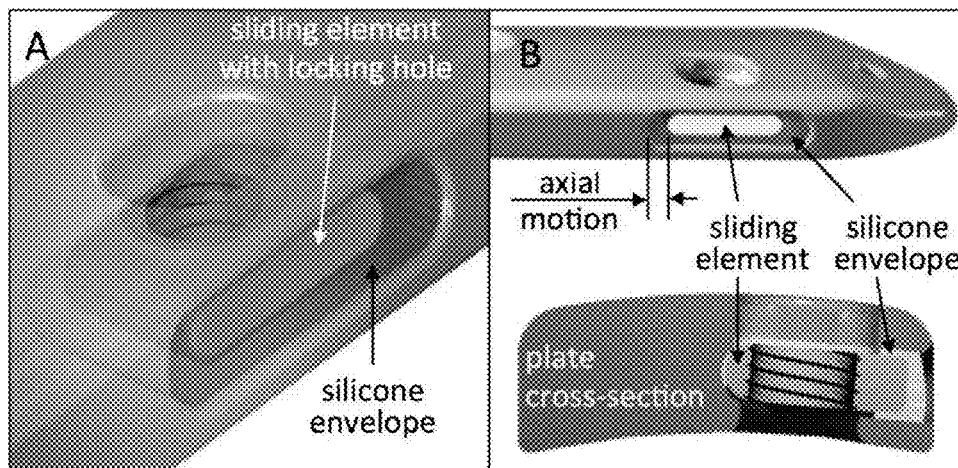
Fig. 21A                    Fig. 21B

FLEXIBLE PLATE FIXATION OF BONE FRACTURES

RELATED APPLICATIONS

The present application is a continuation-in-part of and claims priority to U.S. patent application Ser. No. 13/755,493 filed Jan. 31, 2013, which claims priority to U.S. Provisional Patent Application No. 61/594,560 filed Feb. 3, 2012 and entitled "BONE PLATE FOR OSTEOSYNTHESIS." The present application also claims priority to U.S. Provisional Patent Application No. 62/029,168 filed Jul. 25, 2014 and entitled "FLEXIBLE PLATE FIXATION OF BONE FRACTURES." Each of the disclosures recited above is hereby incorporated by reference in its entirety.

GOVERNMENT INTEREST

This invention was made with government support under AR061201 awarded by the National Institutes of Health. The government has certain rights in the invention.

TECHNICAL FIELD

Embodiments herein relate generally to devices for fixation of a fractured bone. Specifically, the disclosure relates to a bone plate that provides elastic fixation of a fracture. Such elastic fixation enables small motion at the fracture site to promote natural fracture healing by formation of a fracture callus.

BACKGROUND

Osteosynthesis plates for stabilization of bone fractures typically are applied with bone screws. Traditionally, bone screws compress a plate onto the bone surface to provide stable fixation. More recently, locking plates have been introduced, which typically have threaded receiving holes for positive, angle-stable fixation of locking screws that have a correspondingly threaded screw head. These locked plating constructs can provide more durable fixation than traditional non-locked constructs, particularly in weak osteoporotic bone.

However, the inherent stiffness of locked plating constructs causes two clinical challenges. First, it may alter the load distribution in bone, which may either cause bone resorption in load-shielded regions adjacent to the plate, or bone fracture due to implant-induced stress risers. Second, the high stiffness of an osteosynthesis plate construct suppresses relative displacement between bone fragments; however, such interfragmentary motion is important to promote the natural cascade of fracture healing by callus formation. Therefore, overly stiff locking plate constructs may delay or prevent fracture healing, which may also lead to implant breakage or loss of screw fixation in the bone.

Overview

To better illustrate the bone plates disclosed herein, a non-limiting list of examples is provided here:

In Example 1, a device can be provided that includes a bone plate having an upper surface and a bone-facing surface, the bone plate comprising one or more openings extending through the bone plate from the upper surface to the bone-facing surface. The device can further include one or more sliding elements, each sliding element including a fastener receiving hole, wherein the one or more openings at least partially surround a periphery of one of the receiving holes, and wherein the one or more openings are at least partially filled with an elastomer to support elastic suspension of the one or more sliding elements in the bone plate, thereby enabling relative displacement between the one or more sliding elements and the bone plate. The device can further include at least one sensor operable to assess a dynamic parameter of one of the one or more sliding elements within the bone plate.

In Example 2, the device of Example 1 is optionally configured such that the sensor is operable to track a relative position of the sliding element relative to the bone plate.

In Example 3, the device of any one of or any combination of Examples 1-2 is optionally configured such that the sensor is operable to measure displacement of the sliding element relative to the bone plate.

In Example 4, the device of any one of or any combination of Examples 1-3 is optionally configured such that the sensor is operable to measure pressure within the elastomer that is suspending the sliding element in the bone plate.

In Example 5, the device of any one of or any combination of Examples 1-4 is optionally configured such that the sensor is positioned at least partially within the elastomer.

In Example 6, the device of any one of or any combination of Examples 1-5 is optionally configured such that the sensor is operable to measure pressure applied to the bone plate by the elastomer that is suspending the sliding element in the bone plate.

In Example 7, the device of any one of or any combination of Examples 1-6 is optionally configured such that the sensor is self-powered.

In Example 8, the device of any one of or any combination of Examples 1-6 is optionally configured such that the sensor is powered by an external power source.

In Example 9, a bone plate can be provided that includes a plate body having an upper surface and a bone-facing surface, a plurality of openings extending through the plate body from the upper surface to the bone-facing surface, one or more sliding elements each including a fastener receiving hole, each of the one or more sliding elements positioned within a different one of the openings such that the opening at least partially surrounds a periphery of the receiving hole, an elastomer layer at least partially surrounding each of the one or more sliding elements, thereby enabling relative displacement of the sliding element within the plate body, and one or more sensors operable to assess a dynamic parameter of the one or more sliding elements within the plate body.

In Example 10, the bone plate of Example 9 is optionally configured such that each receiving hole is a threaded receiving hole.

In Example 11, the bone plate of any one of or any combination of Examples 9-10 is optionally configured such that each receiving hole is cylindrical.

In Example 12, the bone plate of any one of or any combination of Examples 9-11 is optionally configured such that the elastomer layer has a modulus of elasticity in the range of 0.1-50 MPa.

In Example 13, the bone plate of any one of or any combination of Examples 9-12 is optionally configured such that the elastomer layer is silicone.

In Example 14, the bone plate of any one of or any combination of Examples 9-13 is optionally configured such that the one or more sensors are operable to measure displacement, pressure, or load to capture a presence or magnitude of load transfer between the sensor and the plate body as a means for estimating the progression of fracture healing.

In Example 15, the bone plate of any one of or any combination of Examples 9-14 is optionally configured such that at least one elastomer layer includes an energy generation element to supply transient power to the one or more sensors.

In Example 16, the bone plate of any one of or any combination of Examples 9-14 is optionally configured such that the one or more sensors are powered by an external power source.

In Example 17, the bone plate of any one of or any combination of Examples 9-16 is optionally configured to include one or more accelerometers to determine acceleration of the plate body or one or more of the sliding elements.

In Example 18, the bone plate of Example 17 is optionally configured to include a first accelerometer operably coupled to the plate body and a second accelerometer operably coupled to one of the sliding elements.

In Example 19, the bone plate of Example 18 is optionally configured such that the first and second accelerometers provide feedback to determine a relative acceleration of the sliding element with respect to the plate body.

In Example 20, a device can be provided that includes a bone plate having an upper surface and a bone-facing surface, the bone plate comprising one or more openings extending through the bone plate from the upper surface to the bone-facing surface. The device can further include one or more sliding elements, each sliding element including a fastener receiving hole, wherein the one or more openings at least partially surround a periphery of one of the receiving holes, and wherein the one or more openings are at least partially filled with an elastomer to support elastic suspension of the one or more sliding elements in the bone plate, thereby enabling relative displacement between the one or more sliding elements and the bone plate. The device can further include at least one sensor operable to measure at least one of displacement, pressure, or load to capture a presence or magnitude of load transfer between the sensor and the bone plate and to estimate the progression of fracture healing.

In Example 21, the device or bone plate of any one of or any combination of Examples 1-20 is optionally configured such that all elements or options recited are available to use or select from.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIG. 2 is a transverse cross-sectional view a sliding element with cylindrical threading, in accordance with various embodiments.

FIG. 4 is a transverse cross-sectional view of a sliding element with conical threading, in accordance with various embodiments.

FIG. 5 is a bottom view of a sliding element and a spring element inside a bone plate shown without a bottom to visualize the sliding element, in accordance with various embodiments.

FIG. 6 is a bottom view of a sliding element and integrated spring element inside the bone plate shown without a bottom to visualize the sliding element, in accordance with various embodiments.

FIG. 7 is a bottom view of a sliding element and integrated spring elements inside the bone plate shown without a bottom to visualize the sliding element in accordance with various embodiments.

FIG. 8 is a sectional view of a sliding element shown in association with a bone screw affixed to a cylindrical bone segment, in accordance with various embodiments.

FIGS. 16A-20B are diagrams and graphs related to a first biomechanical study.

FIGS. 21A-26C are diagrams and graphs related to a second biomechanical study.

DETAILED DESCRIPTION

Figure 1:
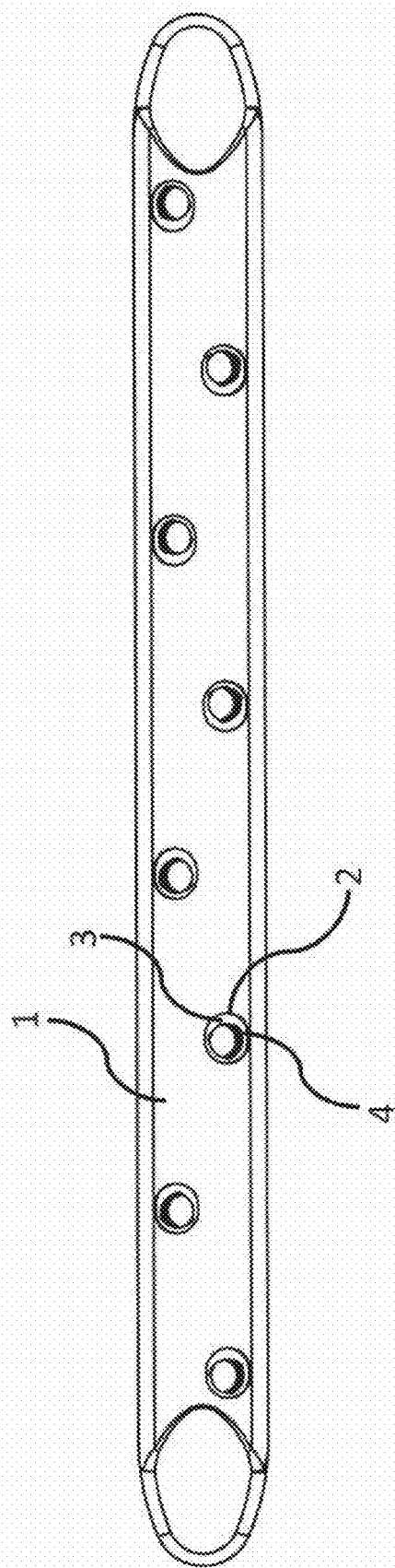
FIG. 1 is a top view of a bone plate in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

In various embodiments, methods, apparatuses, and systems for elastic fixation of a fracture are provided.

Embodiments herein provide an osteosynthesis plate that allows for stable fixation of a bone fracture, while permitting elastic dynamic motion along the longitudinal axis of the bone plate while maintaining stability in all other directions at the fracture site to stimulate fracture healing by callus formation. In an example, a "dynamic" locking plate design is described and tested in which locking screw holes are elastically suspended within a silicone envelope inside the locking plate.

FIG. 1 illustrates a top view of an oblong bone plate 1 with elongated plate holes 2 that are arranged generally along the longitudinal plate axis in a staggered pattern. Sliding elements 3 reside below the surface of bone plate 1 in a manner that the threaded through-hole 4 of the sliding element coincides with the elongated plate hole 2 of bone plate 1. Sliding elements 3 have threaded through-holes 4 for engagement of correspondingly threaded bone fasteners. The through-holes 4 may be oriented substantially perpendicular to the upper surface of bone plate 1. The through-holes 4 may also be angled toward the longitudinal midline of the plate so that a bone fastener inserted into a staggered/offset screw hole will be directed/angled toward the midsection of a bone member to which the plate is coupled. See FIGS. 3 and 10.

FIG. 2 illustrates a transverse cross-section through the bone plate 1 and through the threaded through-hole 4 of sliding element 3. The through-hole 4 is oriented generally perpendicular to the convex upper surface of bone plate 1. The sliding element 3 is generally bar-shaped and of rectangular cross-section. In other embodiments, other cross-sectional shapes may be used, such as square, oval, curved, or a curved rectangle that approximates the cross-sectional shape of the plate. The sliding element is comprised of any medically acceptable material, such as but not limited to a metal like titanium or stainless steel. Sliding element 3 is located in a correspondingly shaped recess 5 that extends to the bottom plate surface 6 and that extends toward the upper plate surface 7 without penetrating through upper plate surface 7 in order to preserve the bending strength of the plate. As shown in FIG. 2, the recess for the sliding element extends through to the bottom plate to the bottom surface, and the sliding element is subsequently retained in the plate with a bottom cover 9. Recess 5 is lined with a low-friction member 8 to reduce friction and wear between the sliding element 3 and recess 5. The low friction member is any medically acceptable material, such as, but not limited to a polymer, such as PEEK (Polyether ether ketone). Other exemplary biocompatible polymers with a low coefficient of friction may be used, such as UHMWPE (Ultrahigh molecular weight polyethylene). Alternatively, the space between the sliding element and the recess may be filled with a silicone derivative that provides a hyper-elastic interface, which may serve to reduce friction and/or to provide an elastic suspension of the sliding element in the recess.

Sliding element 3 is retained inside plate 1 by a bottom cover 9, which is rigidly connected by laser welding, press-fit, or comparably reliable bonding means to plate 1 after insertion of the sliding element. Therefore, sliding element 3 is constrained within bone plate 1 to prevent slider motion perpendicular to the longitudinal axis of bone plate 1. The sliding element 3 may be coupled to a bone member 10 with a locking bone screw 11, which may be a screw that has a threaded screw shaft 12 and a threaded screw head 13 (See FIG. 3)). One preferred locking screw has the same thread outer diameter and thread pitch at the screw head 13 and screw shaft 12. While screw head 13 and screw shaft 12 have the same pitch, i.e. slope of the revolving helix, screw shaft 12 has a single helix and screw head 13 has three helices that simultaneously revolve around the core diameter. This arrangement allows for a larger core diameter in screw head 13 compared to screw shaft 12, making the thread appear denser. This arrangement also has the advantage that the screw shaft is engaged in the threaded hole 14 of sliding element 3 throughout screw insertion. It therefore provides a means to rigidly connect sliding element 3 to bone member 10 at a given elevation over the bone surface without having to compress the sliding element or bone plate against the bone surface. It furthermore prevents screw head 13 from being compressed against sliding element 3 rather than engage into sliding element 3. Positive locking of the bone screw in sliding element 3 is provided by end cap 15 of the screw head 13, which is compressed against the upper surface of sliding element 3.

FIG. 4 illustrates an alternative embodiment of through-hole 14, wherein the threaded hole 14 in the sliding element is conical. This will enable positive locking of a correspondingly threaded conical screw head in the sliding element 3.

FIG. 5 illustrates a bottom view of bone plate 1 without bottom cover 9 to visualize sliding element 3. The longitudinal dimension of the sliding element 3 is less than the corresponding longitudinal dimension of recess 5. This difference in longitudinal dimension determines the permissible axial motion of sliding element 3 relative to plate 1. This controlled range of axial motion ranges from 0.2-2 mm, preferably from 0.3-1 mm. A spring element, such as spring 22, forces sliding element 3 into a defined resting positing by application of an effective spring pre-load in the range of 1-100 N, preferably 5-50 N. If the sliding element 3 is exerting a force against the pre-load of spring element 22, motion of the sliding element relative to the plate is initiated (linear motion along the longitudinal axis of the bone plate). Upon removal of the force, sliding element 3 returns to its resting position by the spring force. One example of pre-loading a spring element is as follows. To preload the spring element, during assembly the spring element is compressed before or when the sliding element and/or spring element is inserted into the bone plate.

FIG. 6 illustrates an alternative embodiment of a spring element, in which a spring element is integrated into, or is part of the sliding element 3 (as opposed to a separate spring) by means of a series of elongate spring fingers 23 and channels 24. Channels 24 transform a portion of the sliding element 3 into an elastic spring element.

FIG. 7 illustrates yet another alternative embodiment of a spring element, in which channels 24 are introduced at opposite sides of sliding element 3. Channels 24 transform opposing sides of sliding element 3 into elastic spring elements, which elastically suspend the threaded screw hole 14 inside recess 5, and which allow bi-directional translation of the threaded through-hole 14 from its unloaded center position.

FIG. 8 illustrates a longitudinal cross-sectional view of an embodiment of sliding element 3 shown in association with a bone screw 11 affixed to a cylindrical bone segment 10. Spring 22 is recessed in a cylindrical hole 17 in sliding element 3. Recess 5 is lined with a low-friction layer 8. Locking screw 11 fixes sliding element 3 in a manner that plate 1 is not compressed onto the bone surface 18. In an alternative embodiment using non-locking screws, the plate may be compressed on the bone surface.

Figure 9:
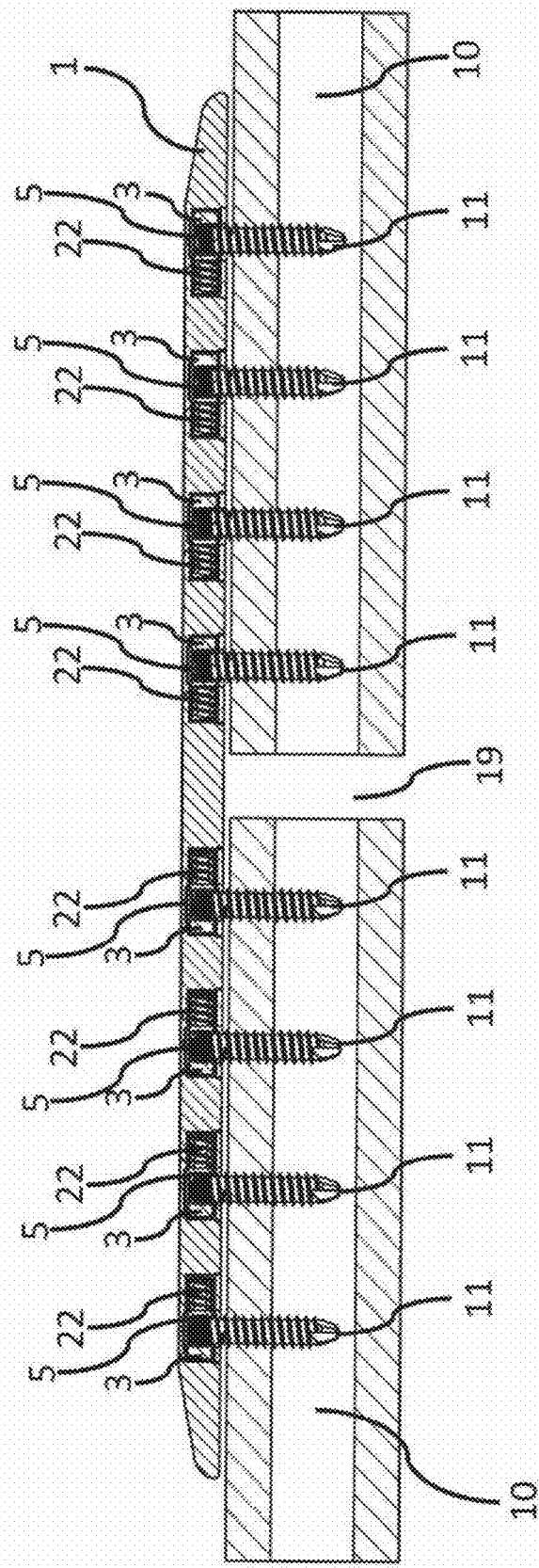
FIG. 9 is a sectional view of a bone plate shown in association with bone screws affixed to two corresponding segments of a cylindrical bone, in accordance with various embodiments.

FIG. 9 illustrates a cross-sectional view of bone plate 1 that is elastically fixed to two corresponding segments of a cylindrical bone 10 with bone screws 11. Springs 22 in sliding elements 3 are located toward the fracture site 19. Application of external compressive force acting upon bone segments 10 will therefore induce translation/movement of sliding elements 3 relative to plate 1, which in turn will induce translation of the bone segments 10 parallel to the longitudinal axis of plate 1. This will generate symmetric motion between the surfaces at fracture site 19 within a controlled motion envelope. The amount of fracture site motion is controlled by the maximal extent of slider translation inside recess 5 of plate 1. Hence, based on the stiffness and pre-load of the spring elements, external compressive force in excess of a predetermined threshold of between 100-1000 N, preferably 200-800 N will not yield additional motion of sliding elements 3 inside the plate. If the pre-load and stiffness of the spring elements are selected to be sufficiently small, the sliding elements will reach their maximal permissible displacement at an external compressive force that is sufficiently low to prevent excessive plate bending, which otherwise could lead to excessive friction, wear, or jamming of sliding members 3 inside their recess.

Elastic coupling of a bone plate to a bone by means of elastically suspended sliding elements may be applied to one or more bone segments of a fractured bone, while other bone segments may be fixed to the same bone plate using standard bone fasteners, such as non-locking or locking screws.

Figure 10:
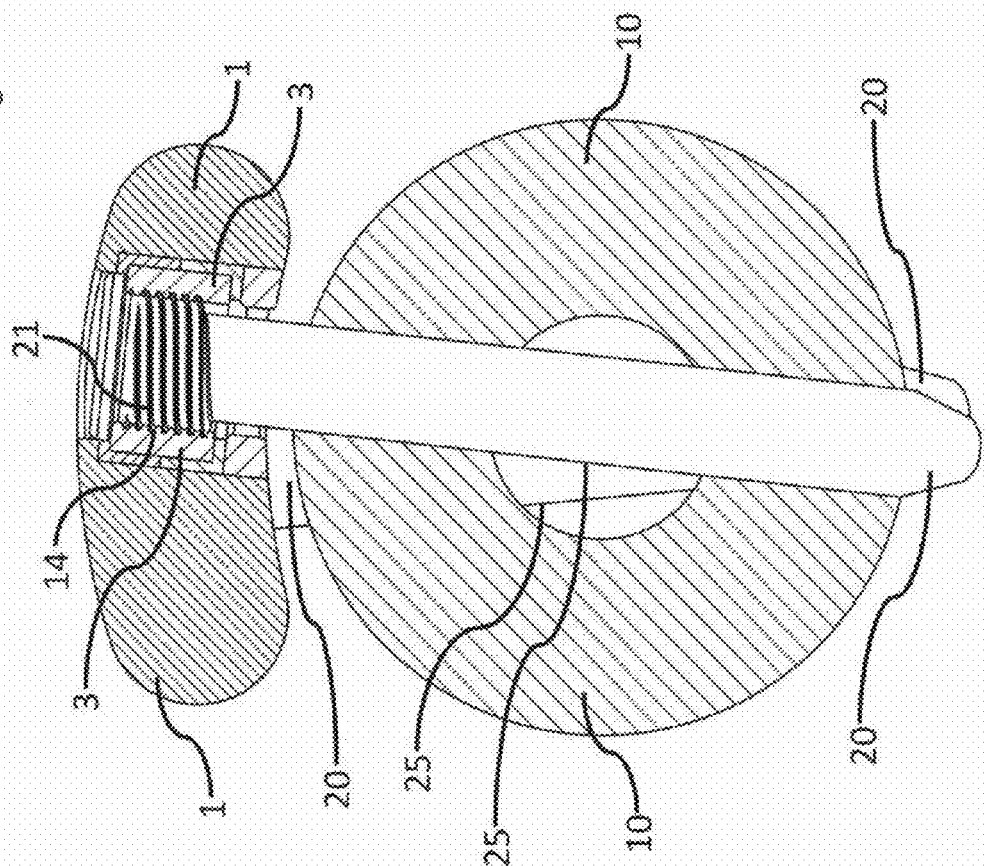
FIG. 10 is a cross-sectional view of a bone plate affixed with non-collinear locking pegs to a cylindrical bone segment, in accordance with various embodiments.

FIG. 10 illustrates a cross-section of bone plate 1 in association with a cylindrical bone 10, wherein plate 1 is affixed to bone 10 with multiple non-collinear bone pegs 20. Bone pegs 20 have a threaded head 21 and are positively locked into the correspondingly threaded through-hole 14 of sliding element 3. Bone pegs 20 have a smooth shaft 25 for multi-planar fixation in the bone, wherein the smooth shaft prevents transmission of forces acting in direction of the peg longitudinal axis onto the sliding element 3.

Figure 11:
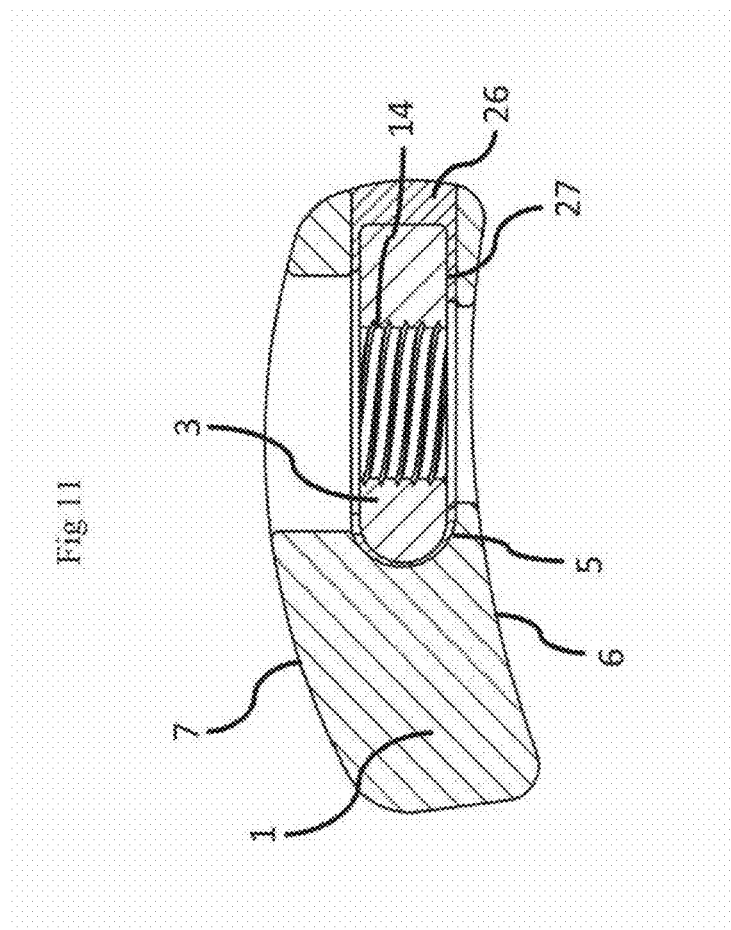
FIG. 11 is a transverse cross-sectional view of a bone plate and sliding element with cylindrical threading and an elastomer lumen suspending said sliding element inside the bone plate, in accordance with various embodiments.

FIG. 11 illustrates a transverse cross-section of bone plate 1 through the threaded through-hole 14 of sliding element 3. The sliding element 3 is at least partially enclosed in recess 5. In certain embodiments, the sliding element is enclosed at the top, bottom, and towards the plate center, but in certain embodiment is actually exposed on the side. By leaving it open on one side, the sliding element can be dropped into place and the silicone can be molded and thus, one would not have to weld a plate over it. In this embodiment, recess 5 is created through the side of bone plate 1 and extends through to the bottom plate surface 6 and that extends toward the upper plate surface 7. Sliding element 3 is suspended within recess 5 by an elastomer lumen 26. The elastomer lumen 26 may be selectively bonded to portions of recess 5 and/or sliding element 3 to affect a desired elastic constraint of the sliding element 3 relative to bone plate 1. For example, in one embodiment, the surface 27 of the sliding element 3 is bonded to the elastomer lumen or elastic material. FIG. 11 shows the situation where the sliding element is restrained against motion. In addition to preventing metal-on-metal contract and abrasive wear, this elastic confinement of the sliding element facilitates engagement of threaded screw heads into the sliding element, especially in the case where a screw is inserted not exactly parallel to the axis of the screw hole in the sliding element.

Figure 12:
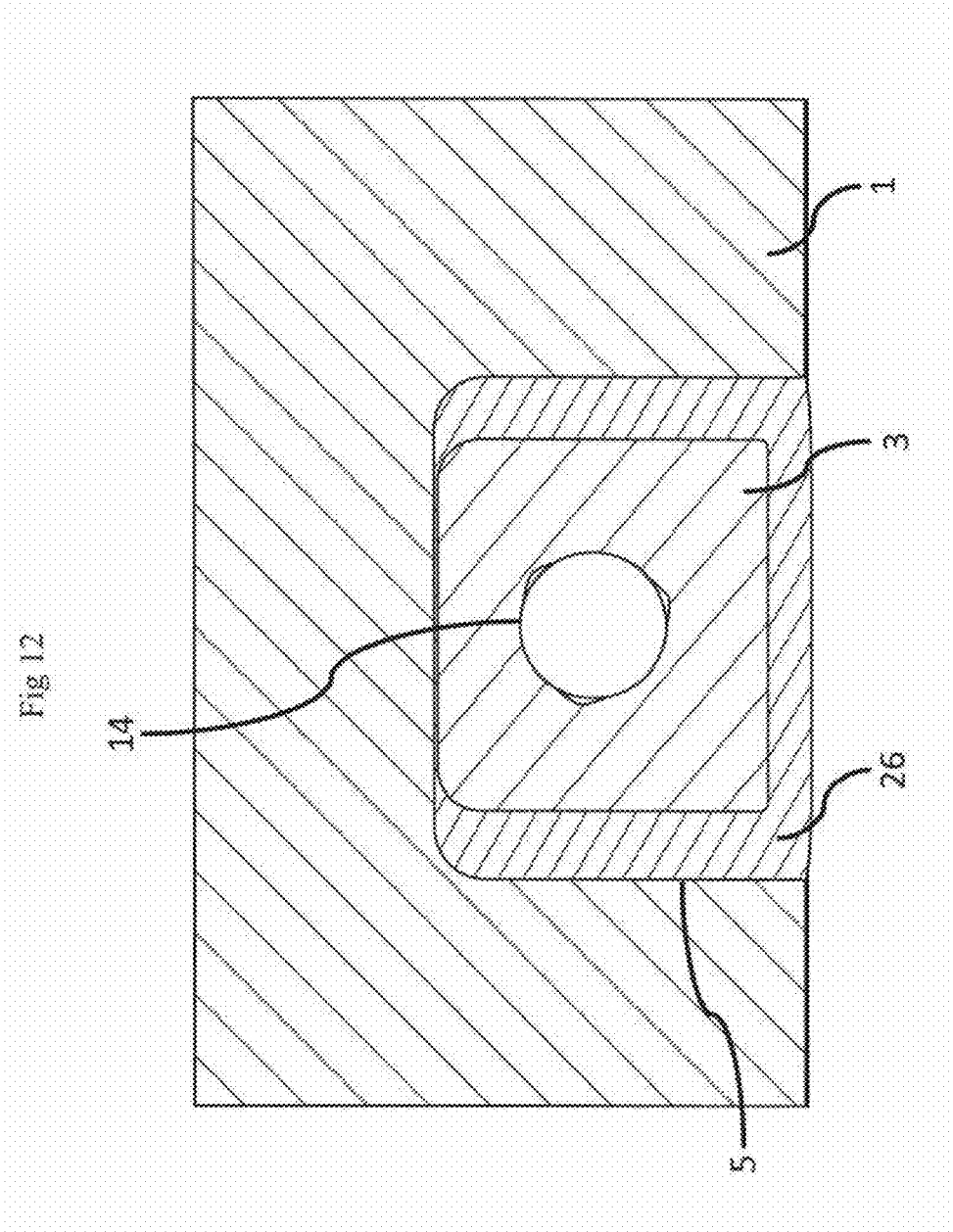
FIG. 12 is a bottom view of a sliding element and elastomer lumen within a slot in the side of the bone plate shown without a bottom to visualize the sliding element in accordance with various embodiments.

FIG. 12 illustrates a bottom view of bone plate 1 without the bottom to visualize sliding element 3 with threaded through-hole 14. Sliding element 3 is enclosed in recess 5 created in the side of bone plate 1 by an elastomer lumen 26 that preferentially allows for longitudinal motion. This figure shows an embodiment where the longitudinal dimension of the sliding element 3 is less than the corresponding longitudinal dimension of recess 5. This difference in longitudinal dimension determines the permissible motion of sliding element 3 relative to plate 1. This controlled range of motion ranges from 0.1-2 mm, preferably from 0.3-1 mm. In the embodiment shown, sliding element 3 does not extend to the outside surface of bone plate 1. FIG. 12 shows the elastomer 26 between the edges of the sliding element 3 and the recess area 5. In other embodiments, the elastomer is an elastomer lumen 26 that surrounds or encases the sliding element 3.

Figure 13:
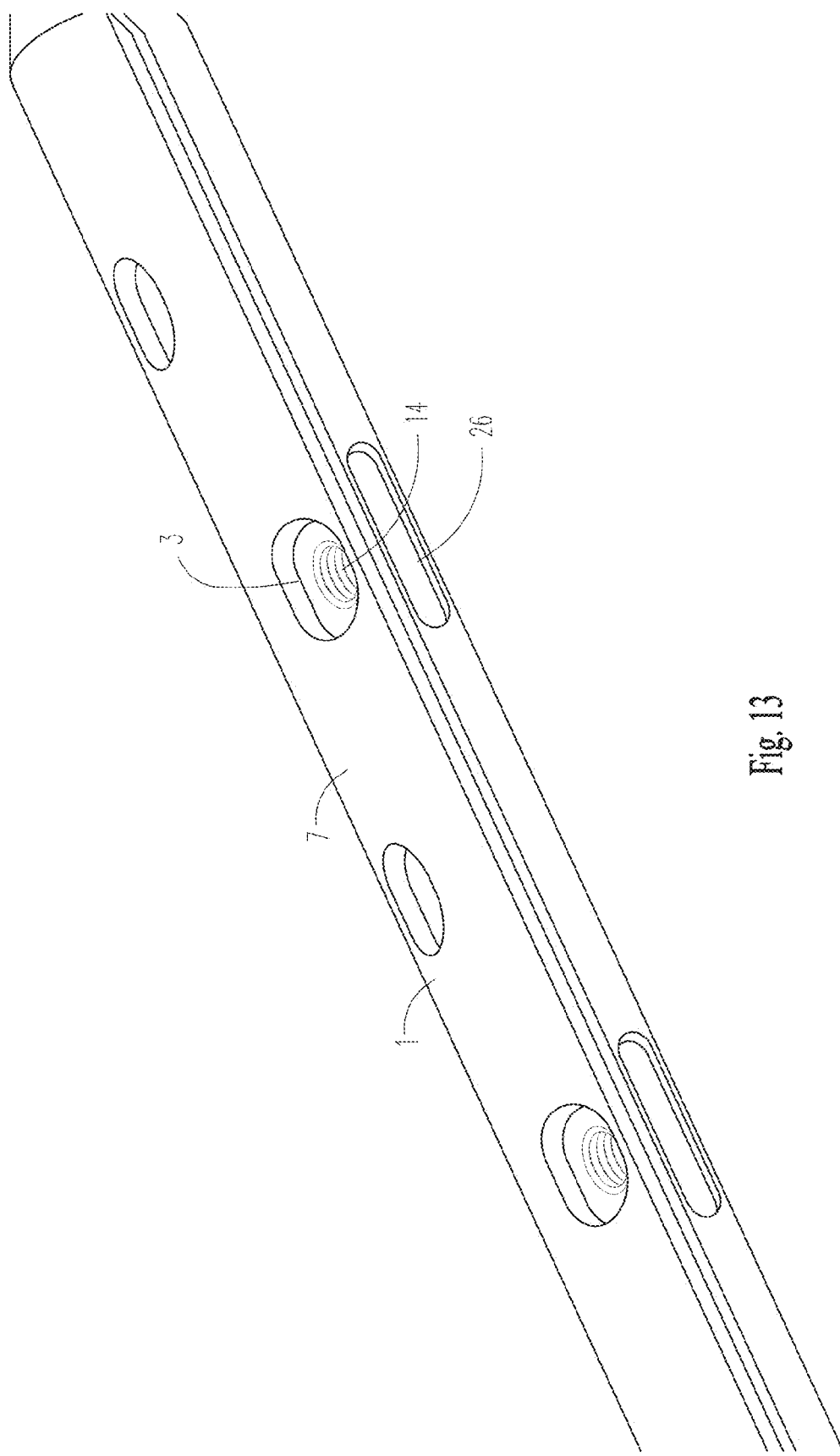
FIG. 13 shows a top view of a bone plate in accordance with various embodiments.

FIG. 13 illustrates a three dimensional view of the bone plate 1 with a top surface 7 and a sliding element 3 with a threaded through-hole 14. This figure shows a recess on the "side of the bone plate" (i.e. not the top surface or the bone facing surface) through which the sliding element 3 and elastomer lumen 26 can be inserted.

Figure 14:
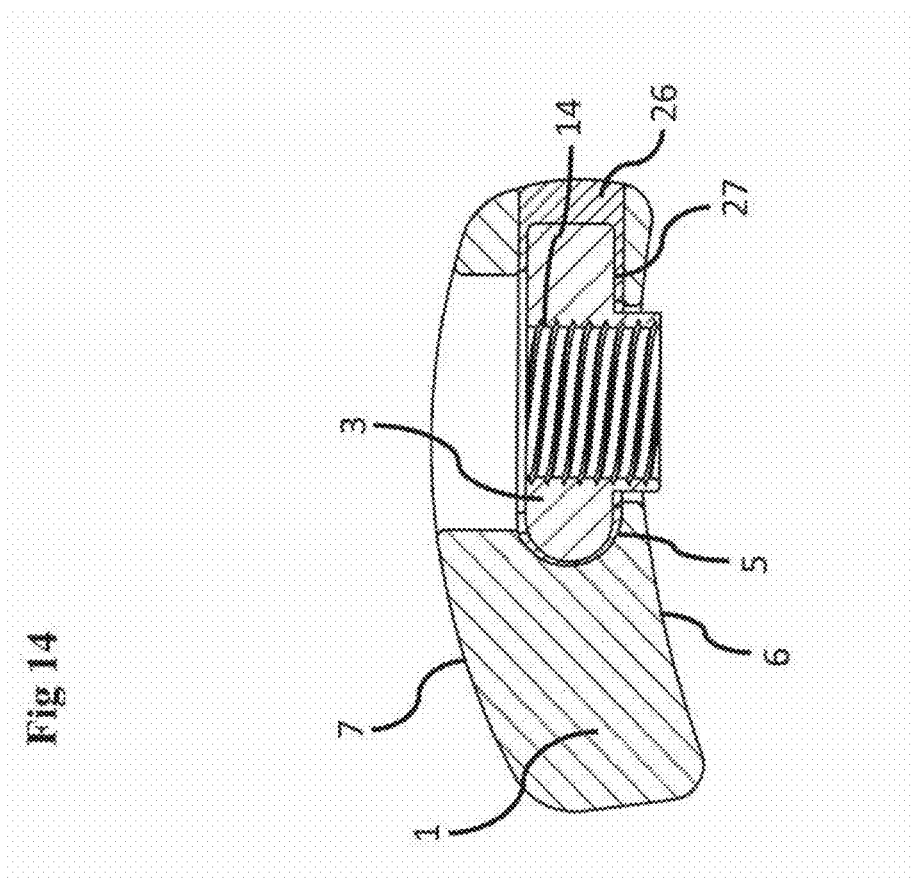
FIG. 14 shows a transverse cross-sectional view a sliding element with cylindrical threading, in accordance with various embodiments.

FIG. 14 shows the sliding element 3 protruding down past the bottom surface 6 of the bone plate 1. The sliding element 3 with a threaded through hole 14 resides in the recess 5. The elastomer lumen 26 is shown surrounding the sliding element 3. This figure shows the internal sliding element 3 is at least partially enclosed within a cavity in the side of the bone plate (i.e. a cavity that is not the bone facing or top facing surface). This figure is designed to show a part of the slider that extends below the bottom surface. The cavity is still in the side of the plate. The surface 27 of the sliding element 3 is bonded to the elastomer lumen or elastic material.

In an embodiment, there is provided a bone plate having an outer surface and a bone-facing surface, the bone plate comprising internal sliding elements, wherein each sliding element contains a threaded receiving hole for bone screws or pegs that have a correspondingly threaded screw head. The sliding elements undergo controlled displacement parallel to the longitudinal axis of the plate but are substantially constrained against displacement perpendicular to the longitudinal axis of the plate. The bone screws with threaded heads can be rigidly fixed to the threaded receiving holes in the sliding elements without compressing the bone plate onto the bone surface. Therefore, a bone segment can be securely fixed to the bone plate, while retaining the ability for controlled displacement parallel to the long axis of the bone plate. The amount of displacement is controlled by the motion envelope of the sliding elements within the bone plate.

The sliding element is generally bar-shaped and of rectangular cross-section. In other embodiments, other cross-sectional shapes may be used, such as square, oval, curved, or a curved rectangle that approximates the cross-sectional shape of the plate. The sliding element just needs to be sized and shaped to fit into the recess of the plate and sized to allow the desired amount of motion. The sliding element is comprised of any medically acceptable material, such as but not limited to a metal like titanium or stainless steel.

The sliding elements may be elastically suspended in the plate by means of a spring element that determines the amount of translation of the sliding element relative to the plate in response to a load acting in a longitudinal direction of the plate. This elastic suspension enables dynamic motion between adjacent bone segments affixed to the bone plate in response to weight bearing of the plate-bone fixation construct. The spring element may be a spring that is separate from the sliding element or the spring element may be part of the sliding element. In other embodiments the spring element is an elastomeric material.

Elastic fixation of the bone to the plate through load-responsive sliding elements enables controlled and symmetric motion at the fracture site, which is known to promote fracture healing by callus formation. Furthermore, elastic fixation enhances load distribution between fixation points, which reduces stress concentrations and thereby enhances construct strength. Elastic fixation furthermore reduces bone resorption and porosis caused by stress-shielding due to overly rigid fixation constructs.

Elastic fixation may be through the use of an elastomer. The elastomer may positively adhere at least to a portion of the plate or the sliding element surface to affect a desired elastic constraint of the sliding element relative to the bone plate.

In certain embodiments, the elastomer is free of voids (e.g. air pockets) or is substantially free of voids. In other embodiments the elastomer has voids which can further reduce the effective stiffness of the system by increasing the compressibility of the elastomer.

The elastomer can be any medically suitable elastomer, such as, but not limited to silicone. In certain embodiments, the elastomer has a modulus of elasticity in the range of 0.1-50 MPa, which allows for the desired amount of movement/elasticity. In certain embodiments the elastic modulus and formulation of the elastomer material may differ within the elastomer, for example, which might be the case if two different elastomers are used or if different thicknesses or viscosities of elastomers were used.

In certain embodiments, the elastomer comprises an elastomer lumen that surrounds or encases the sliding element. In other embodiments, the elastomer is between the sliding element and the wall of the recess.

In certain embodiments the sliding element may be removable as a solitary element or in conjunction with the elastomer lumen. In other words, in certain embodiments, the sliding element is assembled into the plate and the silicone is molded to bond them together. In other embodiments, one could mold and bond the silicone onto the sliding element externally, and then push that component into the plate. In this case, it wouldn't be bonded to the plate. In another embodiment for an "unloaded," modular bone plate, a surgeon can insert either an elastic sliding element, a non-elastic locking element, or a non-locking element In certain embodiments, the elastic suspension of the sliding element in the plate is achieved by means of two or more spring elements that determine an amount of bi-directional translation of the sliding element relative to the plate in response to a load in a longitudinal direction of the plate.

In certain embodiments, the spring elements are comprised of discrete springs. In certain embodiments the spring elements are comprised of integrated springs formed by an elastic structure or material that is part of the sliding element.

In certain embodiments the spring elements are comprised of integrated springs formed by an elastic structure or material that is part of the plate segment adjacent to the sliding element.

In certain embodiments the spring elements are formed by an elastic material (elastomer) that is applied between the sliding element (shown as 3 in FIG. 12) and the plate (1).

In certain embodiments, the spring elements are formed by an elastic material (elastomer) lumen that encases or surrounds the sliding element. For example the elastomer is not between the walls of the recess and the edge of the sliding element but is also on top and below the sliding element.

In one embodiment, a sliding element is suspended between two or more spring elements (such as shown, for example in FIG. 7). This configuration enables elastic displacement in two opposing directions. FIG. 7 shows an embodiment where two spring elements are integral to the sliding element. In another embodiment the spring elements may be separate from the sliding element. In another embodiment, the spring elements may be a combination of a separate spring element and an integral spring element. In other embodiments the spring element may be the elastomer or elastomer lumen. In other embodiments, there may be a combination of a spring element such as a separate spring and an elastomer. For example, one side of the sliding element could have a spring (separate or integral) and on the other side of the sliding element, the spring element could be an elastomer.

In certain embodiments, there may be a combination of discrete or integral spring elements with elastomeric spring elements. For example a discrete and/or integral spring element and the sliding element may be surrounded by an elastomer lumen. Or there may be a combination of a discrete or integral spring element and elastomeric material between the wall of the recess and the sliding element.

In certain embodiments, the elastic suspension of the sliding element in the plate is achieved by means of a spring element that holds each sliding element in a defined resting position, and that determines an amount of uni-directional translation of each sliding element relative to the plate in response to a load in a longitudinal direction of the plate.

In certain embodiments, the bone fracture plate is comprised of more than one (in certain embodiments more than one and in certain embodiments, more than two) through hole, each through hole having a sliding element and a spring element. In certain embodiments the bone fracture plate has all the same shaped and same material sliding elements and spring elements. In certain embodiments, the bone fracture plate has different shaped and/or different material sliding elements and/or different spring elements. For example, certain sections of the plate may have discrete spring elements where other sections of the plate may have spring elements integral to the sliding element and other sections may have elastomeric material spring elements or other areas of the plate may employ a combination of discrete, integral and/or elastic material spring elements.

In another embodiment, a single spring element is used to hold the sliding element in a defined resting position. This ensures a stable position of the sliding element during insertion of a bone screw. Subsequent loading of the fixation construct (such as what happens when a patient applies weight or force to the bone that has the fracture) initiates motion of the sliding element, whereby the onset of motion may be determined by the pre-load of the spring element. Upon load removal, the sliding element returns to its defined resting position.

In another embodiment, the sliding element may be partially or fully embedded in a low-friction layer, such as a polymer membrane. This arrangement reduces friction and wear between the sliding element and the plate.

In another embodiment, the sliding elements and corresponding fixation holes are configured in a staggered arrangement. See for example FIGS. 1, 3, and 10. Compared to sliding elements that are arranged along a straight line, this staggered fixation increases the stabilization of the fixation construct when subjected to torsional loading.

In certain embodiments one or more sliding elements extend past the bone-facing surface of the plate to elevate the plate body over the bone surface when the receiving hole is being compressed onto the bone surface with a non-locking bone screw, which, in conjunction with the elastic suspension of the sliding element, enables controlled relative motion between the plate and the bone surface. See FIG. 14.

In certain embodiments, the internal sliding element is at least partially enclosed within a cavity in the side of the plate. FIG. 11 shows the sliding element enclosed within a cavity in the side of the plate.

In another embodiment, the threaded receiving hole in the sliding element is conical. This enables positive locking of a correspondingly threaded conical screw head in the sliding element.

In another embodiment, the threaded receiving hole in the sliding element is cylindrical and is used in conjunction with bone screws that have the same thread outer diameter and thread pitch at the screw head and screw shaft. This has the advantage that the screw shaft is engaged in the threaded hole of the sliding element throughout screw insertion. This embodiment thereby prevents the screw head from being compressed against the sliding element. Ensuring that the screw head readily engages into the threaded hole of the sliding element also prevents pre-loading of the sliding element inside the bone plate.

Figure 3:
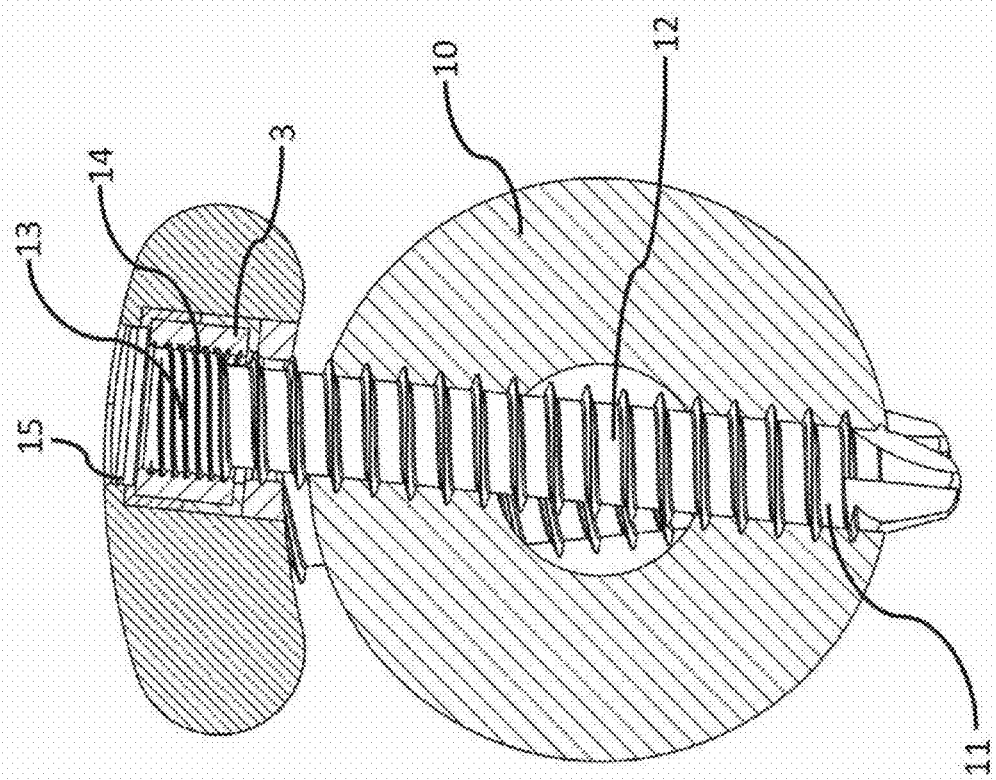
FIG. 3 is a transverse cross-sectional view of a bone plate shown affixed with a bone screw to a cylindrical bone member, in accordance with various embodiments.

In certain embodiments there are a plurality of bone screws (see FIGS. 3 and 9, for example). In certain embodiments, the device further comprises one or more non-collinear bone pegs with a threaded head and a smooth peg shaft (see FIG. 10, for example). In another embodiment, one or more sliding elements may be connected to a bone using pegs with threaded heads that positively engage with the threaded hole of sliding elements. The use of locking pegs in place of locking screws reduces the risk of pre-loading the sliding element inside the plate. To enhance the fixation strength, locking pegs may be inserted in a multi-planar configuration, wherein at least two threaded holes of sliding elements have central axes that are not collinear.

In certain embodiments, the plate incorporates threaded and/or non-threaded screw holes.

In another embodiment, sliding elements may only be located in a certain segment of the bone plate, while another segment of the bone plate has threaded or non-threaded holes (as used in the industry). In one embodiment, the spring elements and sliding elements are located in one segment of the plate, while another segment of the plate has threaded or non-threaded holes without spring elements and sliding elements. The bone plate segment with standard threaded holes or standard non-threaded holes without spring elements and sliding elements (as used in the industry)(referred to herein and in the claims as static receiving holes) allows compression and rigid fixation of the plate to the bone surface, whereas the bone segment with sliding elements/spring elements enables elastic fixation of a corresponding bone segment, which retains the ability to achieve interfragmentary motion in response to intermittent loading of the fixation construct. For example, on one side of the fracture, the bone plate may comprise elastic suspension using the spring elements and sliding elements whereas on the corresponding bone segment on the other side of the fracture, the bone plate comprises static receiving holes (and does not comprise elastic suspension). Also in certain embodiments sliding elements/spring elements and static receiving holes can be used together in the same section of the bone plate. For example, every other hole may be a static receiving hole (and the other holes are the elastic suspension through holes). In other embodiments, there is a mixture of elastic suspension (using sliding elements and spring elements) and static receiving holes, which mixture may be the same throughout the whole bone plate across the fracture. In other embodiments, the mixture of static receiving holes and elastic suspension may vary within the plate. For example, one side of the fracture may have more elastic suspension and few static receiving holes whereas on the other side of the fracture, there may be more static receiving holes than elastic suspension. In other words, different parts of the bone plate may use different combinations of each.

In another embodiment, sliding elements and one or more screw holes may be combined in the same plate segment. This allows temporary affixation of the plate to the bone surface using a standard non-locking screw to facilitate application of locking screws into sliding elements.

The present invention also provides methods of fixing a bone fracture using a flexible plate. In certain embodiments the method comprising: approximately aligning the fractured bone members; and applying a bone plate across the fracture with a plurality of bone fasteners that rigidly connect to receiving holes in a plurality of sliding elements that are elastically suspended in the bone plate. The sliding elements are configured to permit controlled translation parallel to the longitudinal axis of the bone plate, while substantially preventing displacement perpendicular to the longitudinal axis of the plate. The bone screw is rigidly fixed to the sliding elements without compressing the bone plate or sliding element onto a bone surface.

In certain embodiments the receiving holes are suspended to preferentially permit translation relative to the plate along the longitudinal axis of the plate while substantially constraining motion of the one or more receiving holes in a direction that is perpendicular to an upper or bone-facing surface of the bone plate.

In certain embodiments the spring elements act as elastic springs that suspend receiving holes in a neutral position relative to the plate in absence of load application and that enable controlled elastic translation of the receiving hole relative to the plate in response to load application.

In certain embodiments the flexible elements dampen the transmission of impact load between the plate and the bone member to enhance the stability of the fixation construct.

In certain embodiments the flexible elements enhance the distribution of load transfer between multiple fixation elements associated with a single bone segment. With standard static plates, typically one screw is loaded more than the rest since the alignment is not perfect. Using the elastic suspension of the present invention (elastically suspended sliding elements), the load is distributed across all of the screws since they are allowed to displace, and the elastic elements even out the loading.

In certain embodiments the flexible elements prevent at least in part direct contact between the receiving hole and the plate to reduce surface wear and material fatigue.

In certain embodiments the elastic suspension of two or more receiving holes and the plate is practiced on one side of a fracture, while the corresponding bone segment is attached to static receiving holes.

In certain embodiments the elastic suspension of two or more receiving holes and the plate is practiced on both sides of a fracture.

In certain embodiments the elastic suspension of two or more receiving holes and the plate provides for a substantial reduction in axial stiffness of the fixation constructs in the range of 40-90% compared to a bone plate construct with static receiving holes.

In certain embodiments one or more flexible elements contain a sensor to measure displacement, pressure, or load to capture the presence or magnitude of load transfer between a receiving element and the plate as a means for estimating the progression of fracture healing. For example, a sensor can be embedded to help determine when the bone is healed. For example, if the sensor measures displacement, then one would expect as the bone healed, the displacement of the parts would decrease with time. If the sensor measured load, one would expect the load on the plate to diminish as the bone healed.

In certain embodiments the elastomer material comprises an elastomer lumen, and wherein the elastomer lumen of one or more of the flexible elements contains a means for energy generation to supply transient power to said sensor.

In certain embodiments, any of the bone plates described above with reference to FIGS. 1-14 can be designed as a "smart" bone plate capable of measuring one or more dynamic parameters after implantation. One example of a parameter that can be measured is motion at the fracture gap, which can be used to assess bone healing. Compared to standard monolithic locking plates, dynamic bone plates with a sliding element suspended and isolated from the plate are uniquely designed to allow for the incorporation of one or more sensors.

Figure 15:
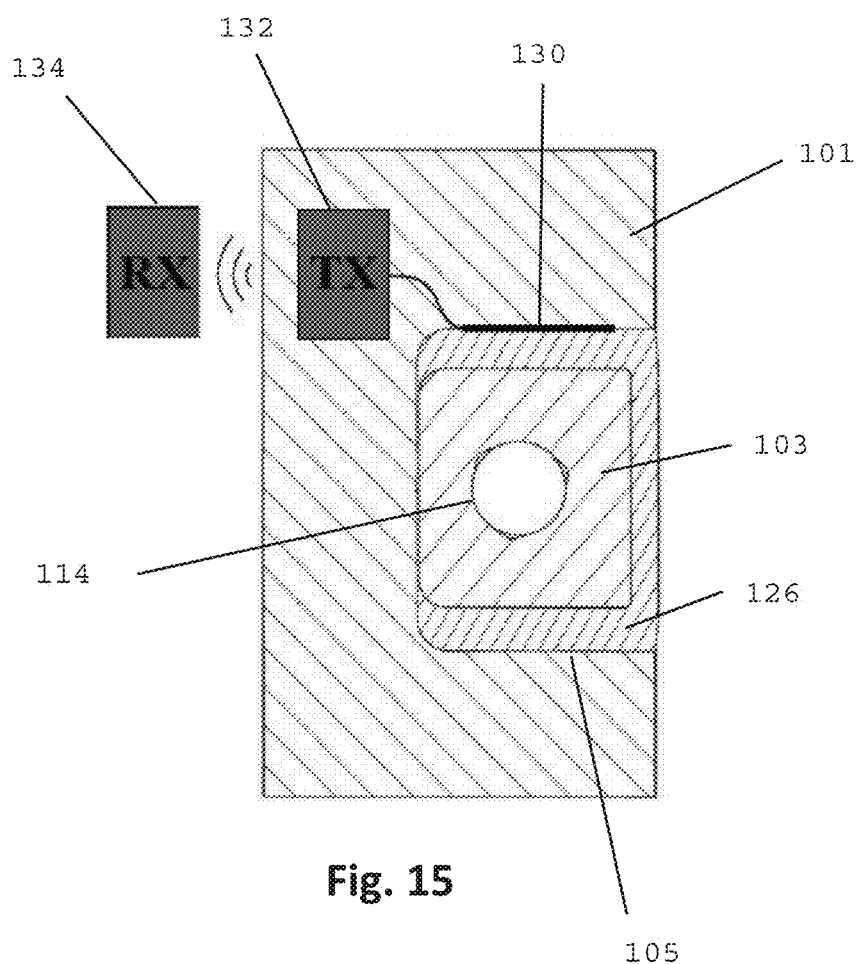
FIG. 15 is a diagram of a "smart" bone plate capable of measuring one or more parameters after implantation.

FIG. 15 illustrates a cross-section view of a bone plate 101 similar to the bone plate 1 illustrated in FIG. 12. As shown in FIG. 15, the bone plate 101 can include a sliding element 103 with a threaded through-hole 114. The sliding element 103 can be enclosed in a recess 105 created in a side of the bone plate 101 by an elastomer lumen 126 that allows for longitudinal motion. As illustrated in FIG. 15, the longitudinal dimension of the sliding element 103 is less than the corresponding longitudinal dimension of the recess 105. This difference in longitudinal dimension determines the permissible motion of the sliding element 103 relative to the plate 101.

As further illustrated in FIG. 15, the bone plate 101 can include one or more sensors 130 operably coupled to the sliding element 103 or the body of the bone plate 101. The sensor 130 can be operably coupled to a transmission element 132, which can be configured to communicate with a receiver element 134 located external to the bone plate 101. In an example, the transmission element 132 can also acts as a receiver, and the receiver element 134 can also act as a transmitter. Such devices are commonly known as transceivers. Any suitable wireless communication means can be used including, but not limited to, radio-frequency telemetry, radio-frequency identification, Bluetooth, Zig-Bee, near field communication, intrabody communication, and the like. The transmitter element 132 can include a power source integrated therein, or a power source can be incorporated into the bone plate 101 separate from the transmitter element 132. Alternatively or additionally, an external power source can be integrated into the receiver element 134 or provided as a separate external element.

The sensor 130 can comprise any suitable sensor for measuring a dynamic parameter of the bone plate 101, the sliding element 103, the elastomer lumen 126, or combinations thereof. Thus, in an example, one or more sensors 103 can be incorporated into the bone plate 101, the sliding element 103, the elastomer lumen 126, or combinations thereof. The sensor 103 can be self-powered, or powered by an external power source. In an example, the sensor 130 can be incorporated into the bone plate 101 in a suitable manner to assess motion of the sliding element 103 relative to the bone plate 101 for the purpose of assessing the performance of the bone plate 101. In another example, the sensor 130 can be configured to measure the relative position of the sliding element 103 with respect to the bone plate 101. In another example, the sensor 130 can be configured to directly measure displacement of the sliding element 103. In yet another example, the sensor can be configured to measure pressure within the elastomer lumen 126 or applied by the elastomer lumen 126 to the adjacent body of the bone plate 101 as a means to indirectly assess motion of the sliding element 103. When assessing motion, the sensor 130 can be configured to measure longitudinal motion of the sliding element 103. Motion in other directions can also be assessed by the sensor 130.

Instead of or in addition to the sensor, the bone plate 101 can include at least one accelerometer. In an example, two accelerometers can be used, with one disposed on or positioned within the body of the bone plate 101 and one disposed on or positioned within the sliding element 103 or the elastomer lumen 126, to determine the relative acceleration of the sliding element 103.

In order to further explain some of the benefits of the dynamic bone plates described herein, two Examples are provided below. Specifically, Example 1 sets forth the results of a first biomechanical study to show how elastically suspended screw holes in a locked osteosynthesis plate can dampen impact loads. Example 2 sets forth the results of a second biomechanical study to show how dynamic locking plates can provide symmetric axial dynamization to stimulate fracture healing.

EXAMPLE 1

Summary: The high stiffness of locking plate constructs can contribute to iatrogenic bone fracture and implant fatigue. Conversely, impact damping by means of elastic fixation is a principal engineering strategy to increase the durability of load-bearing structures exposed to prolonged dynamic loading. The present Example evaluated impact damping provided by a "dynamic" locking plate design in which locking screw holes are elastically suspended within a silicone envelope inside the locking plate.

In a biomechanical study, impact damping was assessed for three distinct fixation constructs applied to bridge a 10 mm fracture gap of a femoral diaphysis surrogate: a standard locking plate, a dynamic locking plate, and an Ilizarov ring fixator. First, the three fixation constructs were characterized by determining their axial stiffness. Subsequently, constructs were subjected to a range of axial impact loads to quantify damping of force transmission.

Compared to a standard locking plate construct, dynamic plating constructs were 58% less stiff (p<0.01) and Ilizarov constructs were 88% less stiff (p<0.01). Impact damping was found to correlate inversely with construct stiffness. Compared to standard plating constructs, dynamic plating constructs and Ilizarov constructs were found to dampen the transmission of impact loads by up to 48% (p<0.01) and 74% (p<0.01), respectively. Thus, the results of the biomechanical study demonstrated that a lower construct stiffness correlated with a superior damping of impact loads, whereby dynamic locking plates provided significantly greater impact damping compared to standard locking plates.

Background: Osteosynthesis plate constructs have to sustain prolonged load transmission across a fracture until the fracture healing process gradually restores physiological load transfer. Clinically, this plate osteosynthesis represents a race between fracture healing and fixation failure, whereby prolonged or excessive loading increases the risk of loosening or fatigue failure of the fixation construct.

Elastic suspension is a principal engineering strategy to increase the durability of constructs that are exposed to prolonged dynamic loading. In case of impact loading, elastic suspension can act as a shock absorber that dampens the load magnitude by distributing the impact energy over a prolonged time period to prevent structural damage. Specific to fracture fixation, traditional Ilizarov fixators elastically suspend fracture segments inside external circular frames by means of thin Kirschner wires. Conversely, modern locking plates represent a highly rigid fixation method, whereby locking screws with threaded screw heads are positively locked into threaded plate holes. These locking plate constructs can achieve improved fixation in weak, osteopenic bone compared to traditional non-locking constructs. However, in absence of elastic fixation, locking plate constructs also exhibit a considerable risk of bone fracture and implant fatigue since their rigid fixation has shown to induce stress concentrations at the screw-bone and screw-plate interface.

To enable elastic fixation with locking plates, the present inventors developed a "dynamic" locking plate, in which the locking screw holes are elastically suspended within a silicone envelope inside the locking plate. The present inventors hypothesized that the elastic suspension provided by a dynamic locking plate can dampen impact loads transmitted through the osteosynthesis construct compared to contemporary, rigid locking plates. For historic comparison to a highly flexible fixation system, the present inventors furthermore hypothesized that the tension-wire suspension of Ilizarov fixators provides superior damping of impact loads compared to rigid fixation with locking plates. The goal of the biomechanical study was to delineate the correlation between the stiffness of osteosynthesis constructs and their ability to dampen the transfer of impact loads. Such impact damping behavior may provide clinical benefits, whereby a reduction in peak loading could potentially mitigate the risk of implant fracture, bone fracture, or fixation failure.

Description of Method: In the biomechanical study, impact damping was assessed for three distinct fixation constructs applied to bridge a 10 mm fracture gap in a femoral diaphysis surrogate: a standard locking plate, a dynamic locking plate, and an Ilizarov ring fixator. First, the three fixation constructs were characterized by determining their axial stiffness under quasi-static loading. Subsequently, constructs were subjected to a range of axial impact loads representative in magnitude to physiological loading. Impact damping was quantified by determining the magnitude and duration of the force transmitted through each construct in response to well-defined impact loads.

Figures 16A, 16B:
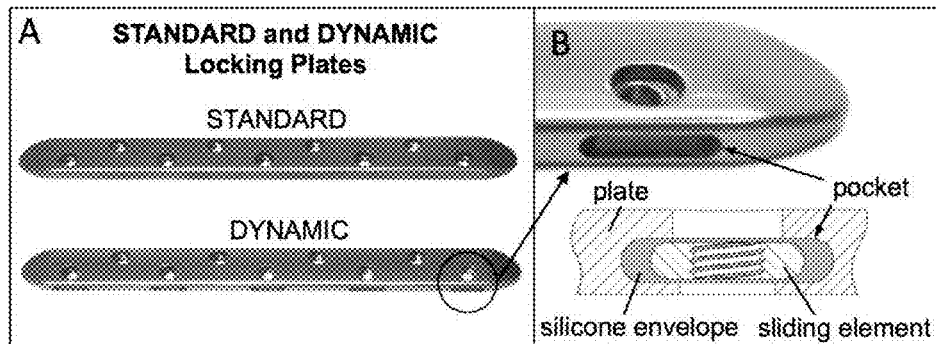

The standard locking ("standard") and dynamic locking ("dynamic") plates had an identical cross-sectional geometry, representative of a typical large fragment plate for fixation of femur fractures, as shown in FIG. 16A. The standard and dynamic plates had 9 holes, were 204 mm long, 18 mm wide, 6 mm thick, and were made of Ti6Al4V ELI titanium alloy (F136-13, 2003). The only difference between the standard and dynamic plates was that the locking holes of the dynamic plates were integrated in individual sliding elements that were elastically suspended in a silicone envelope inside lateral plate pockets, as shown in FIG. 16B. The pocket geometry allowed approximately 1 mm of axial translation of the sliding elements but closely constrained all remaining degrees of freedom. Hence, the elastic suspension enabled controlled axial motion across the fracture gap in response to compressive loading, while providing stable fixation in response to bending and torsional loading. The silicone suspension was transfer-molded from long-term implantable medical-grade silicone elastomer (HCRA 4750, Applied Silicone, Santa Paula, Calif., USA) of 50 A Durometer hardness. The standard and dynamic plates accommodated the same 5.0 mm diameter bicortical self-tapping locking screws.

Figures 17A, 17B, 17C:
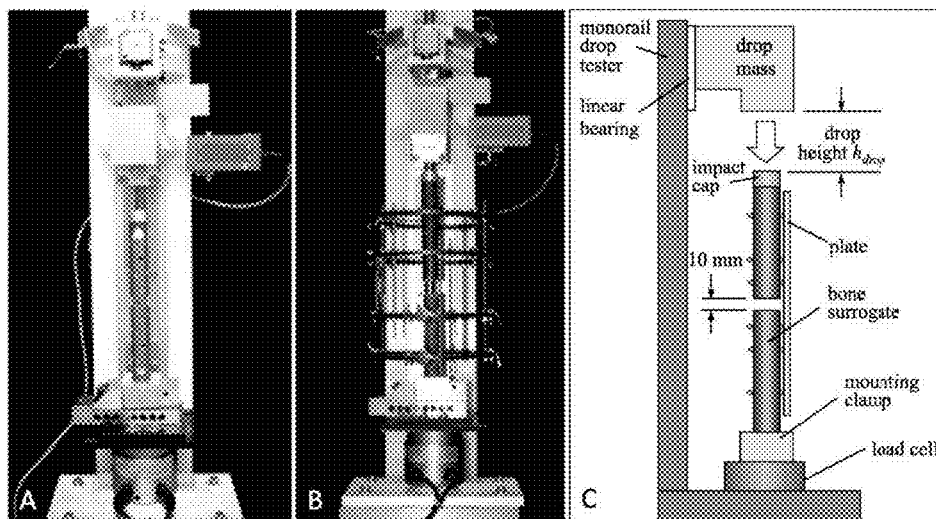

To minimize interspecimen variability, the plates were evaluated in cylindrical strong bone surrogates representative of the femoral diaphysis (3403-10, Sawbones, Vashon, Wash., USA) with a diameter of 27 mm and a wall thickness of 7 mm. The plates were applied to bridge a 10 mm wide osteotomy gap in the midsection of the 270 mm long diaphysis surrogate. This gap osteotomy simulated the biomechanical constraints of a comminuted fracture that relies on full load transfer through the osteosynthesis construct due to a lack of bony continuity at the fracture site. The standard and dynamic plates were applied with three screws on each side of the osteotomy gap, placed in locking holes 1, 3, and 4 from the plate ends, with the central locking hole located over the osteotomy gap remaining empty, as shown in FIG. 17A. The Ilizarov construct consisted of two 180 mm diameter rings above and below the osteotomy gap, as shown in FIG. 17B. Each ring was applied with two 1.8 mm Kirschner wires, tensioned to 130 kg.

Construct stiffness and impact damping was assessed on three specimens for each of the three groups (standard, dynamic, and Ilizarov). Construct stiffness was assessed in a servo-hydraulic material test system (Instron 8800, Norwood, Mass.). Constructs were rigidly connected to a load cell distally and to the actuator proximally. The actuator applied static axial compression in 50N increments up to 1000 N. Construct stiffness was extracted by dividing each load increment by the corresponding actuator displacement increment.

Impact damping was tested with a mono-rail drop test system for application of controlled, scalable impacts to the fixation construct, as shown in FIG. 17C. The drop test system was designed and verified to comply with an impact testing standard (F1446-13, 2013), and correlated with impact test simulations of prior biomechanical studies. Axial impacts were induced by vertical drops of a 2.0 kg mass from increasing drop heights $h_{drop}$ of 5, 10, 20, 40 and 60 mm, which in turn induced impacts ranging in energy $E_I$ from 0.1-1.2 Joules. Impacts were centered onto the proximal end of the vertically aligned diaphyseal constructs. The distal end of the constructs was rigidly fixed to the center of a uni-axial load cell (Instron 12619, Norwood, Mass.). This load cell recorded the impact force $F_T$ that was transmitted through the osteosynthesis construct. The $F_T$ signal was recorded at a sample rate of 20 kHz with a data acquisition system (PCI-6221, National Instruments, Austin, Tex., USA), and processed with a 600 Hz low-pass filter as specified by impact test standard (F1446-13, 2013). Finally, the $F_T$ signal was post-processed to determine the peak force $F_{T,peak}$ transmitted during impact and the impact duration $t_I$. Impact duration was evaluated from the onset of the $F_T$ signal until $F_{T,peak}$. Three constructs of each group were tested at each of the five impact drop heights $h_{drop}$ ranging from 5 to 60 mm.

For statistical analysis of impact force results, $F_{T,peak}$ and $t_I$ values were compared between the three fixation constructs using ANOVA at a significance level of α=0.05, followed by a Bonferroni adjusted pair-wise comparison to determine significant difference between construct pairs.

Figures 18A, 18B:
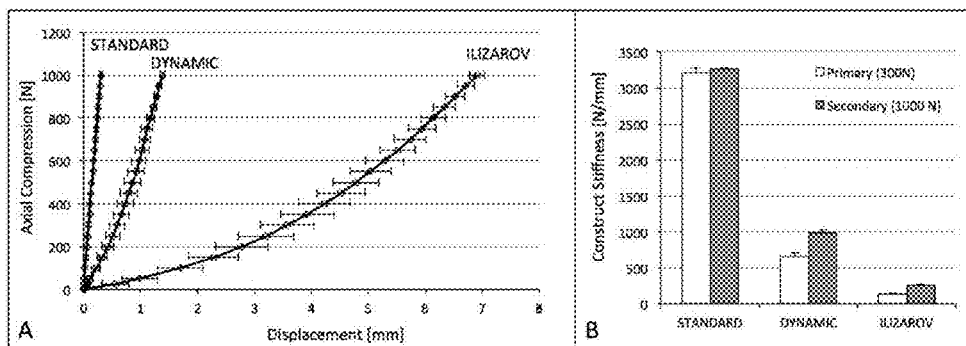

Results: Axial load-displacement histories up to 1,000 N compression yielded a constant stiffness for standard constructs, but a progressively increasing stiffness for dynamic and Ilizarov constructs, as shown in FIG. 18A. Specifically, standard plating constructs were comparably stiff at 300N loading (3,213 N/mm) and at 1000N loading (3,265 N/mm). The mean stiffness of dynamic plating constructs increased from 649 N/mm at 300 N loading to 992 N/mm at 1,000 N loading. The mean stiffness of Ilizarov constructs increased from 138 N/mm at 300 N to 260 N/mm at 1,000 N. At 300 N compressive loading, dynamic plating constructs were 58% less stiff (p<0.01) and Ilizarov constructs were 88% less stiff (p<0.01) than standard plating constructs, as shown in FIG. 18B.

Figures 19A, 19B:
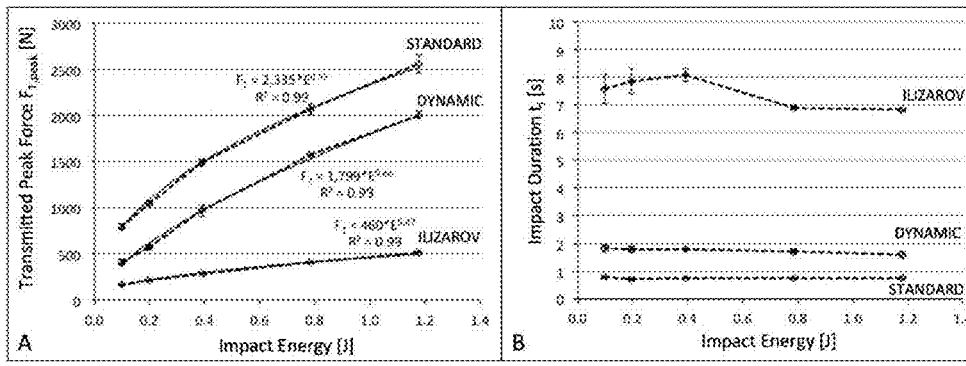

In impact tests, the transmitted force $F_{T,peak}$ increased for increasing levels of impact energy in a power correlation, as shown in FIG. 19A. For a given impact energy level, the stiffest construct induced the highest $F_{T,peak}$ value and therefore permitted the least amount of impact damping. The impact duration $t_I$ was nominally constant for a given fixation construct, irrespective of the impact energy, as shown in FIG. 19B. However, $t_I$ between constructs varied by one order of magnitude, with stiffer constructs yielding shorter impact durations. Mean impact durations were 0.7 s (SD 0.03 s), 1.7 s (SD 0.09 s), and 7.5 s (SD 0.56 s) for standard, dynamic, and Ilizarov constructs, respectively.

Dynamic plating constructs significantly reduced $F_{T,peak}$ compared to standard locking plate by on average 488 N (SD 64 N). Reduction in $F_{T,peak}$ ranged from 48% (p<0.01) at 5 mm drop height to 22% (p<0.01) at the 60 mm drop height, and shown in FIG. 20A. This reduction in $F_{T,peak}$ corresponded to an increase in impact duration $t_I$, as can be seen in a typical force history graph as illustrated in FIG. 20B. The dynamic plating constructs increased $t_I$ compared to standard locking plate constructs by on average 133% (p<0.01).

Ilizarov constructs significantly reduced $F_{T,peak}$ compared to standard locking plates. Reduction in $F_{T,peak}$ ranged from 60% (p<0.01) at 5 mm drop height to 74% (p<0.01) at the 60 mm drop height. Ilizarov constructs significantly increased $t_I$ compared to standard by on average 325% (p<0.01).

Discussion: For fracture fixation, Ilizarov ring fixators provide an inherent damping mechanism by elastic suspension of external fixator rings on wire "spokes." Due to their superior durability, Ilizarov fixators are frequently used for revision surgery when intramedullary nails or plating constructs fail to tolerate the extended weight bearing in case of delayed unions or non-unions.

In contrast, to the knowledge of the present inventors, impact damping mechanisms have not been explored nor implemented in osteosynthesis plates. Plating constructs are typically one order of magnitude stiffer than Ilizarov fixators. Unlike Ilizarov fixators, plating constructs carry a well-recognized risk of inducing iatrogenic bone fracture at the plate end. Modern locking plates induce an even higher stress riser at the plate end, which has shown to reduce construct strength by up to 22% compared to standard non-locking plates. In addition, the incidence of implant fatigue and fixation failure of locking plate constructs has been found to be as high as 12%.

While the use of silicone elastomer in plate osteosynthesis represents a new concept, long-term implantable silicone has been used clinically for a range of permanent implants, such as finger joints. Unlike silicone gel, the silicone elastomer used in finger joints and in the dynamic locking plate of the present biomechanical study is highly biocompatible and bioinert.

Results of the present biomechanical study demonstrated that impact damping elements in dynamic locking plates can significantly reduce load transmission compared to standard locking plates. Impact damping was found to correlate inversely with construct stiffness, whereby the stiffest construct (standard) provided the least amount of damping and transmitted the highest peak force $F_{T,peak}$. The observation that dynamic locking constructs reduced the peak forces while increasing the impact duration is consistent with the damping mechanism of shock absorbers that decrease peak loading by distributing the impact energy over a prolonged impact duration. This impact damping behavior of dynamic constructs may provide clinical benefits, whereby a reduction in peak load transmission could potentially mitigate the risk of implant fracture, bone fracture, or fixation failure. In addition, the elastic fixation of dynamic locking plates reduced the construct stiffness compared to a standard locking plate, which in turn increases the amount of motion induced at the fracture site. Since biologic fracture healing by callus formation is stimulated by interfragmentary motion, the elastic fixation provided by dynamic plating may furthermore support the biomechanical environment required for stimulation of healing.

In conclusion, results of the present biomechanical study demonstrated that fracture fixation constructs with a lower stiffness have a greater potential to dampen the transmission of impact loads. Compared to standard locking plates, dynamic locking plates have a significantly lower stiffness and significantly dampen the transmission of impact loading.

EXAMPLE 2

Summary: Symmetric axial dynamization of locking plate constructs with far cortical locking ("FCL") screws was found to significantly enhance the speed and strength of fracture healing. Because FCL derives dynamization from flexion of elastic screw shafts, it cannot be effectively scaled to short screws required for fractures in small diameter bones. To address this scaling limitation, the present biomechanical study evaluated a new dynamic locking plate that derives symmetric axial dynamization independent of the length of locking screws by elastic suspension of locking holes within the plate being used.

Standard locking ("standard") plate constructs and dynamic locking ("dynamic") plate constructs were tested in a diaphyseal bridge-plating model of the femoral diaphysis to determine the amount and symmetry of interfragmentary motion in response to axial loading, and to assess construct stiffness under axial loading, torsion, and bending. Subsequently, the standard and dynamic constructs were dynamically loaded until failure in axial compression, torsion, and bending to determine construct strength and failure modes. Finally, strength tests were repeated in a validated model of the osteoporotic femoral diaphysis to determine construct strength and failure modes in a worst-case scenario of bridge-plating in osteoporotic bone.

One body-weight (700N) axial loading of standard plating constructs produced asymmetric interfragmentary motion that was over three times smaller at the near cortex (0.1±0.01 mm) than at the far cortex (0.32±0.02 mm). Compared to standard plating constructs, dynamic plating constructs symmetrically enhanced motion by 0.32 mm at the near cortex and by 0.33 mm at the far cortex. Dynamic plating constructs had a 77% lower axial stiffness (p<0.001), a 15% lower torsional stiffness (p=0.03) and a similar bending stiffness (p=0.27) relative to the standard locking constructs. There was no significant difference in strength between dynamic and standard locking constructs under all test conditions, expect under torsion of non-osteoporotic specimens in which dynamic constructs were 21% stronger (p=0.01) than standard constructs.

Dynamic plate constructs were shown to symmetrically enhance interfragmentary motion and deliver controlled axial dynamization, and were found to be at least comparable in strength to standard plate constructs. Thus, dynamic plates can be applied with standard locking screws and symmetrically enhance axial dynamization to promote natural bone healing by callus formation.

Background: Axial dynamization of an osteosynthesis construct can be a deciding factor in the race between fracture healing and failure of the fixation construct. Research over the past 50 years has consistently demonstrated that controlled axial dynamization can improve the speed and strength of fracture healing by dynamically stimulating secondary bone healing via callus formation. The landmark study by Goodship and Kenwright demonstrated that 1 mm axial dynamization delivered over three times stronger healing and over two times faster healing compared to rigid fixation (see Goodship A E, Kenwright J. The influence of induced micromovement upon the healing of experimental tibial fractures. *J Bone Joint Surg Br* 1985; 67-4:650-5). Conversely, there is abundant evidence that deficient fracture motion caused by overly stiff fixation constructs can suppress secondary fracture healing, contributing to delayed unions, non-unions, and fixation failure. Rigid fixation is the principal requirement for primary bone healing, in which anatomic reduction and interfragmentary compression is used to suppress callus formation. However, perfect reduction and absolute stabilization is difficult to achieve and is prone to osteolysis induced by stress shielding. Primary bone healing is also slower and weaker than secondary bone healing and carries a considerable re-fracture risk.

Locking plates provide fixed-angle stabilization, enabling biological bridge-plating techniques that emphasize preservation of blood supply and functional reduction over anatomic reduction and interfragmentary compression. In the absence of anatomic reduction and interfragmentary compression, locked bridge plating constructs rely on secondary bone healing. However, the initial stiffness of locking plate constructs is comparable to conventional plate constructs designed to maximize stiffness for primary bone healing. Locking plate constructs retain their initial stiffness for a prolonged duration, unlike conventional non-locking plates, which undergo gradual loosening over time.

FCL screws or dynamic locking screws ("DLS") permit controlled and symmetric interfragmentary motion by elastic flexion of screw shafts, allowing axial dynamization of locking plate constructs. In a fracture healing study in the ovine tibia, axial dynamization of FCL constructs was found to deliver symmetric callus bridging on all cortical surfaces and yielded 157% stronger healing compared to standard locking plates (see Bottlang M, Lesser M, Koerber J, Doornink J, von Rechenberg B, Augat P, Fitzpatrick D C, Madey S M, Marsh J L. Far cortical locking can improve healing of fractures stabilized with locking plates. *J Bone Joint Surg Am* 2010; 92-7:1652-60). Clinically, a prospective observational study of 31 consecutive distal femur fractures stabilized with FCL constructs reported no implant or fixation failure, an average time to union of 16 weeks, and a non-union rate of 3% (see Bottlang M, Fitzpatrick D C, Sheerin D, Kubiak E, Gellman R, Vande Zandschulp C, Doornink J, Earley K, Madey S M. Dynamic fixation of distal femur fractures using far cortical locking screws: a prospective observational study. *J Orthop Trauma* 2014; 28-4:181-8). While these data support the need and efficacy of axial dynamization of locking plate constructs, FCL and DLS screws cannot be effectively scaled to short screws applicable for fractures in small diameter bones because they require sufficiently long screw shafts for elastic flexion.

To address this scaling limitation, the present biomechanical study evaluated a new strategy, termed dynamic plating, which derives symmetric axial dynamization independent of the type and length of locking screws being used. In one example of dynamic plates utilized in the present biomechanical study, locking holes were elastically suspended within the plate by means of a silicone envelope that controls the amount of permissible axial motion, as shown in FIGS. 21A and 21B. This biomechanical study tested the hypothesis that dynamic plates can provide symmetric controlled axial dynamization while retaining strength comparable to standard locking plate constructs.

Description of Method: Standard locking plate constructs and dynamic locking plate constructs were tested in a diaphyseal bridge-plating configuration under axial compression, torsion and bending. First, stiffness tests of standard and dynamic plate constructs were performed in each principal loading mode in surrogates of the non-osteoporotic femoral diaphysis to determine the amount and symmetry of interfragmentary motion, as well as construct stiffness in axial compression, torsion and bending. Subsequently, constructs were tested to failure in each loading mode to determine their strength and failure modes. Finally, failure tests were repeated in a validated model of the osteoporotic femoral diaphysis to determine construct strength and failure modes in a worst-case scenario of bridge-plating in osteoporotic bone.

The standard and dynamic plates had an identical cross-sectional geometry, representative of a typical large fragment plate for fixation of femur fractures. The standard and dynamic plates had 8 holes, were 204 mm long, 18 mm wide, 6 mm thick, and were made of Ti6Al4V ELI titanium alloy. The only difference between the plates was that the locking holes of the dynamic plates were integrated in individual sliding elements that were elastically suspended in a silicone envelope inside lateral plate pockets, as shown in FIGS. 21A and 21B. Lateral pockets were arranged in an alternating pattern from both plate sides, resulting in a staggered locking hole configuration. The pocket geometry allowed approximately 1 mm of axial translation of the sliding elements but closely constrained all remaining degrees of freedom. Hence, the elastic suspension enabled controlled axial motion across the fracture gap in response to compressive loading, while providing stable fixation in response to bending and torsional loading. The silicone suspension was transfer-molded from long-term implantable medical-grade silicone elastomer (HCRA 4750, Applied Silicone, Santa Paula, Calif., USA) of 50 A Durometer hardness. The standard and dynamic plates accommodated the same 5.0 mm diameter self-tapping locking screws. The plates were evaluated in a standard bridge-plating configuration in femoral diaphysis surrogates with a 10 mm fracture gap. This gap osteotomy simulated the biomechanical constraints of a comminuted fracture that relies on full load transfer through the osteosynthesis construct due to a lack of bony continuity at the fracture site. The plates were applied with three screws placed in the first, second, and third hole from the fracture site. The central locking hole over the osteotomy gap remained empty, yielding a plate span of 36 mm that was bridging the gap. All screws were tightened to 4 Nm with the plate at 1 mm elevation from the surrogate surface using temporary spacers to simulate biological fixation with preservation of periosteal perfusion.

The plates were evaluated in surrogate specimens of the femoral diaphysis to minimize inter-specimen variability and to ensure consistency with prior studies for outcome comparison. Plate evaluation in non-osteoporotic bone was performed on cylindrical strong bone surrogates representative of the medium-size femoral diaphysis (3403-10, Sawbones, Vashon, Wash., USA). Diaphyseal surrogates had a 27 mm outer diameter and 7 mm wall thickness and were made of short fiber reinforced epoxy composite that was validated to replicate the fracture toughness of cortical bone. For plate evaluation in weak bone, a validated model of the osteoporotic femoral diaphysis was used. This model consisted of a 27 mm diameter and 2 mm thick cortex made of reinforced expoxy and a trabecular core machined from 10 pcf (0.16 g/cm$^3$) solid rigid polyurethane foam. To reduce the amount of diaphyseal surrogates required, surrogates were only applied to one side of the bridge plating constructs. On the opposite side, plates were fixed to a reusable aluminum cylinder of 27 mm diameter which isolated construct failure to the surrogate side.

Figures 22A, 22B, 22C:
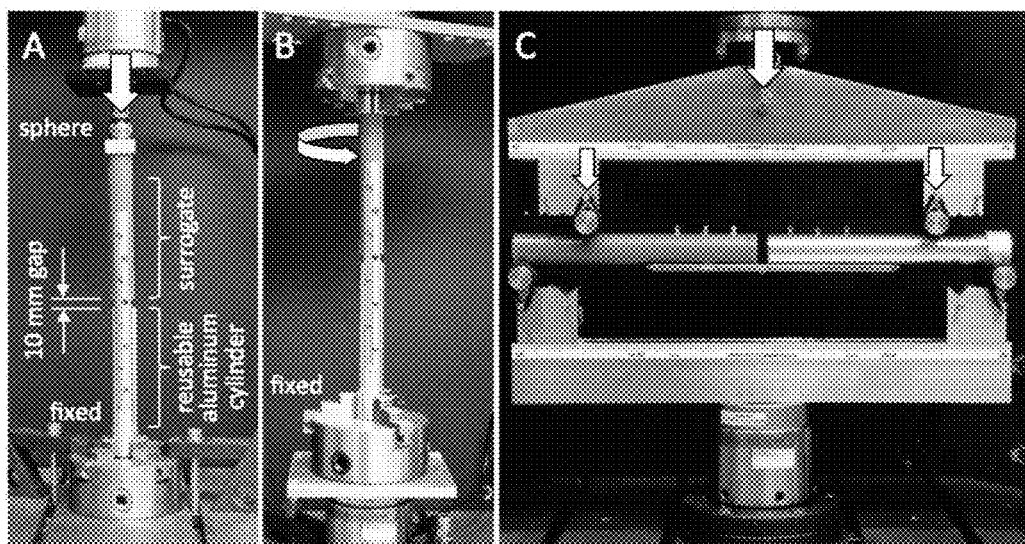

Standard and dynamic plate constructs were tested in axial compression, torsion, and bending with a bi-axial material testing system (Instron 8874, Canton, Mass.), as shown in FIG. 22A. Constructs were tested to failure under each loading mode in three non-osteoporotic and three osteoporotic diaphyseal surrogates, requiring a total of 36 test specimens. Axial compression was applied through a spherical bearing proximally while the distal end of the specimen was rigidly mounted to the load cell to replicate axial loading configurations of prior studies (see Bottlang M, Doornink J, Fitzpatrick D C, Madey S M. Far cortical locking can reduce stiffness of locked plating constructs while retaining construct strength. *J Bone Joint Surg Am* 2009; 91-8:1985-94; Stoffel K, Booth G, Rohrl S M, Kuster M. A comparison of conventional versus locking plates in intraarticular calcaneus fractures: a biomechanical study in human cadavers. *Clin Biomech (Bristol, Avon)* 2007; 22-1: 100-5; and Marti A, Fankhauser C, Frenk A, Cordey J, Gasser B. Biomechanical evaluation of the less invasive stabilization system for the internal fixation of distal femur fractures. *J Orthop Trauma* 2001; 15-7:482-7). Torsion was applied around the diaphyseal shaft axis, as shown in FIG. 22B. Bending was applied in a four-point-bending setup to generate a constant bending moment over the entire plate length, as shown in FIG. 22C. The upper and lower cylindrical supports were separated by 290 mm and 400 mm, respectively. The plate was located on the tension side to induce bending in a gap-closing mode. First, stiffness tests were conducted in non-osteoporotic bone surrogates under axial compression, torsion and bending by loading to 1 KN, 10 Nm and 10 Nm, respectively. Subsequently, construct strength was determined by progressive dynamic loading to failure. After application of a static pre-load $L_{PRE}$, sinusoidal loading with a load amplitude of $L_{DYN}$ was applied at 2 Hz. Every 100 loading cycles, this load amplitude was increased stepwise by $L_{DYN}$ until construct failure occurred. For axial compression, torsion, and bending, pre-loads $L_{PRE}$ of 50 N, 1 Nm, and 1 Nm and stepwise load amplitudes $L_{DYN}$ of 100 N, 1 Nm, and 1 Nm were selected, respectively. This stepwise load increase enabled dynamic loading to failure while ensuring that failure was attained for each construct within a reasonable number (<10,000) of load cycles. Construct failure was defined either by catastrophic fracture or by a subsidence threshold, whichever occurred first. Subsidence $d_S$ represents the non-recoverable collapse after load removal as measured by the actuator position, which is caused by implant bending or loosening. A $d_S$ threshold of 1 mm, 5 degrees, and 1 mm in compression, torsion, and bending, respectively, was deemed indicative of the onset of construct failure in the absence of a catastrophic fracture. Subsidence $d_S$ was assessed from displacement and rotation reports of the test system actuator.

The performance of the standard and dynamic plate constructs was described by their amount and symmetry of axial interfragmentary motion, construct stiffness, construct strength, and failure mechanism. The amount of axial dynamization, termed $d_{AVG}$, was assessed by averaging interfragmentary motion at the near and far cortices in response to incremental axial loading, measured by two digital calipers with 0.01 mm resolution. Symmetry of axial dynamization was assessed by comparison of interfragmentary motion at the near cortex ($d_{NC}$) and far cortex ($d_{FC}$). The stiffness of constructs was evaluated for compression, torsion, and bending. Compressive stiffness was calculated by dividing the applied axial load by the resulting interfragmentary motion $d_{AVG}$. Torsional stiffness was calculated by dividing the torsion amplitude by the amplitude of actuator rotation $\alpha$ around the diaphyseal axis. Torsional stiffness was multiplied by the unsupported specimen length to derive torsional rigidity. Bending stiffness was expressed in terms of flexural rigidity $EI=Fa^2 (3l-4a)/12y$ where F is the total applied force, l=400 mm is the distance between the lower supports, a=55 mm is the distance between the lower and upper support, and y is the displacement of the upper supports. Construct strength was defined as the peak load $L_{MAX}$ during progressive dynamic loading to failure. Failure modes were visually analyzed for presence of hardware failure, fixation failure and bone fracture.

For statistical analysis, stiffness and strength results were compared between the dynamic and standard groups individually for each loading mode. In addition, axial dynamization parameters $d_{NC}$ and $d_{FC}$ at the near and far cortex were compared within groups. Two-tailed, unpaired Student's t-tests at a level of significance of $\alpha=0.05$ were used to detect significant differences.

Figures 23A, 23B:
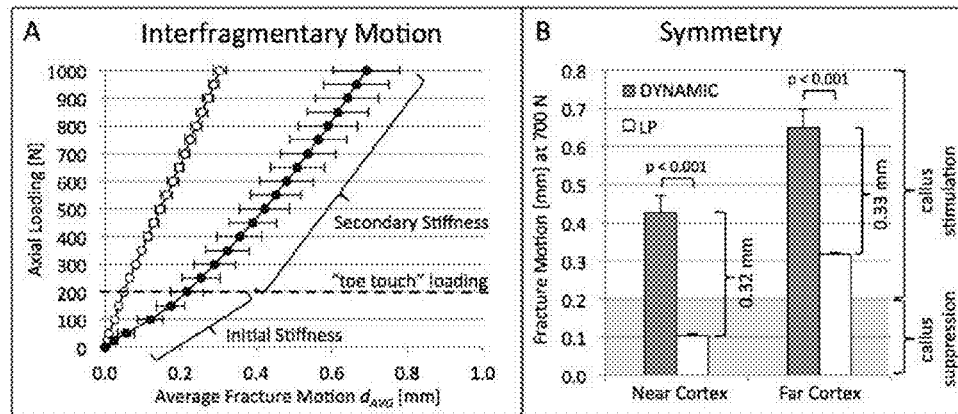

Results: The dynamic constructs generated significantly more interfragmentary motion than the standard constructs by symmetrically enhancing motion at the near and far cortex. At 200 N axial loading representative of "toe-touch" weight-bearing, axial dynamization $d_{AVG}$ in the dynamic constructs (0.22±0.05 mm) was over 4 times higher than in the standard constructs (0.05±0.01 mm), as shown in FIG. 23A. The standard constructs required 700N to achieve 0.2 mm axial dynamization, which represents the minimum motion threshold known to stimulate callus formation. However, this 700N loading of the standard constructs induced asymmetric dynamization, whereby near cortex motion ($d_{NC}$=0.10±0.01 mm) remained below the 0.2 mm stimulation threshold, and was over three times smaller than far cortex motion ($d_{FC}$=0.32±0.02, p<0.001), as shown in FIG. 23B. The dynamic constructs symmetrically improved this dynamization by 0.32 mm at the near cortex and by 0.33 mm at the far cortex as compared to the standard constructs, as shown in FIG. 23B. Even at the maximum load of 1,000N applied for stiffness assessment, near cortex motion in the standard constructs ($d_{NC}$=0.15±0.01 mm) remained below the 0.2 mm threshold, and was over three times smaller than near cortex motion in the dynamic constructs ($d_{NC}$=0.53±0.08, p<0.001).

Figures 24A, 24B, 24C:
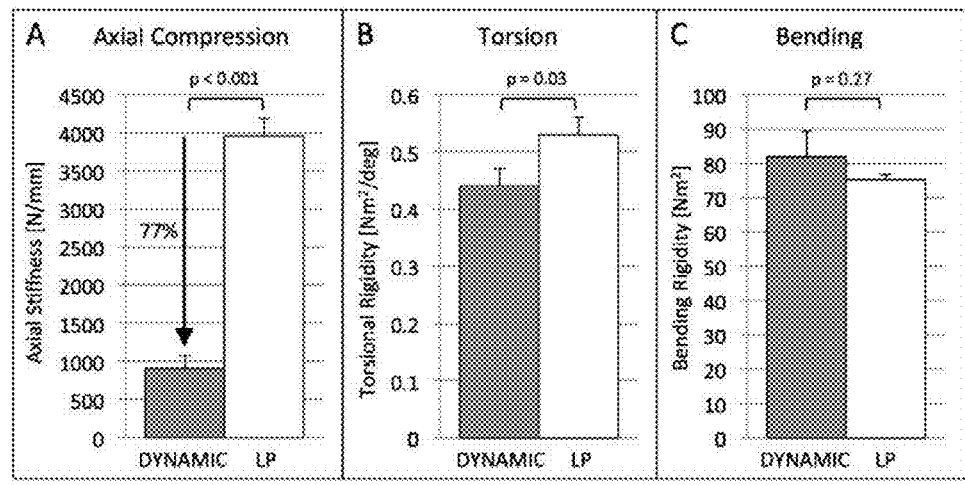

In axial loading, the initial stiffness of the dynamic constructs (911±165 N/mm) was 77% lower than that of the standard constructs (3,960±230 N/mm, p<0.001), as shown in FIG. 24A. At elevated loading above 200N, the dynamic constructs exhibited a secondary stiffness of 1,732±140 N/mm. Under torsion, the torsional rigidity of the dynamic constructs (0.44±0.03 Nm$^2$/°) was 15% lower that that of the standard constructs (0.53±0.03 Nm$^2$/°, p=0.03), as shown in FIG. 24B. In bending, the bending rigidity of the dynamic constructs (81.9±7.6 Nm$^2$) was comparable to that of the standard constructs (75.3±1.3 Nm$^2$, p=0.27), as shown in FIG. 24C.

Figures 25A, 25B, 25C:
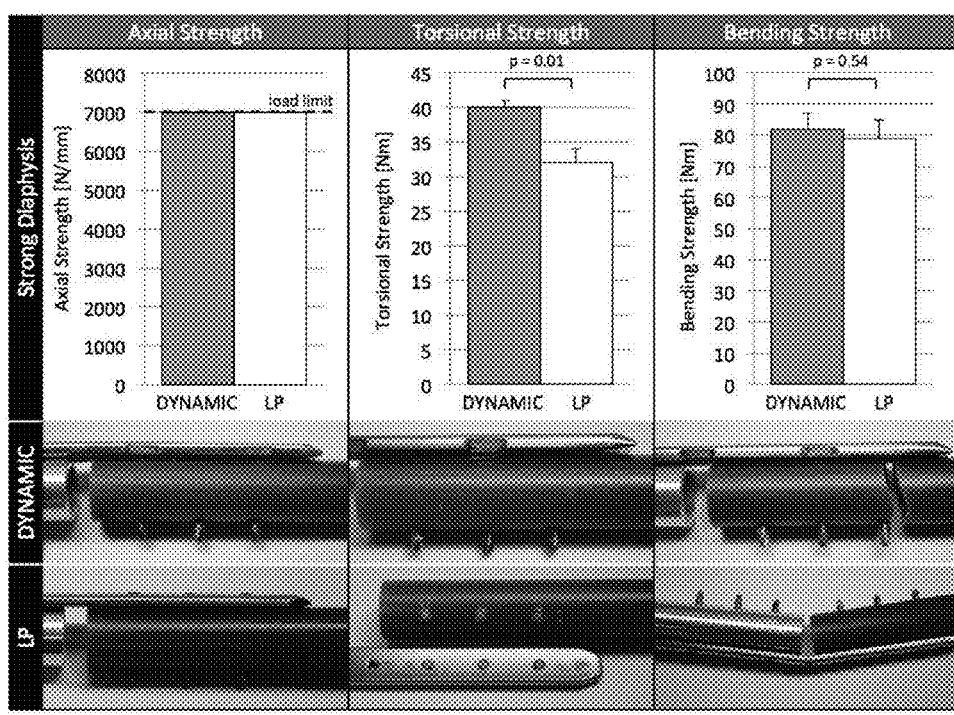

With reference to FIG. 25A, in axial compression, all dynamic and standard constructs sustained the upper load limit of 7,000 N, or approximately 10 times body-weight loading, without failure. Under torsion, the dynamic constructs sustained a 25% higher load (40±1 Nm) than the standard constructs (32±2 Nm, p=0.01), as shown in FIG. 25B. The dynamic constructs failed by breakage of the plate pocket housing the sliding element. The standard constructs failed by breakage of all three screws between the elevated plate and the bone due to repetitive screw bending during cyclic torsion. In bending, the strength of the dynamic constructs (82±5 Nm) was comparable to that of the standard constructs (79±6 Nm, p=0.54), as shown in FIG. 25C. The dynamic constructs failed by surrogate fracture through the screw hole at the plate end. The standard constructs failed by plate bending through the central screw hole centered over the fracture gap.

Figures 26A, 26B, 26C:
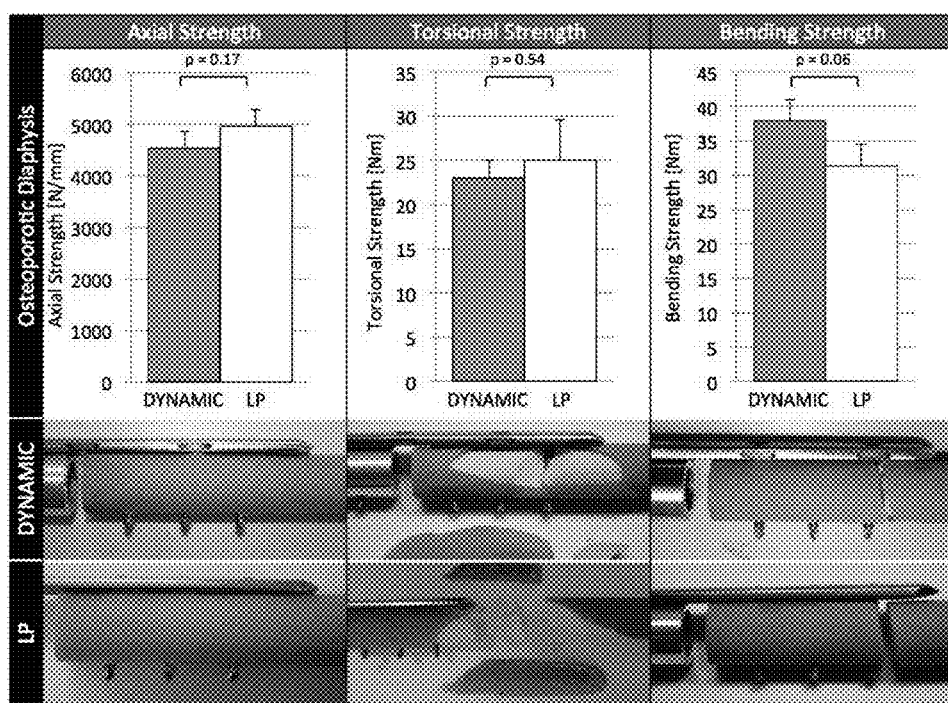

With reference to FIG. 26A, in axial compression, the strength of the dynamic constructs (4,533±322 Nm) was comparable to that of the standard constructs (4,967±322 Nm, p=0.17). All constructs failed by a combination of screw bending and screw subsidence in the near cortex, which induced cortical fracture lines between screw holes.

Under torsion, the strength of the dynamic constructs (23±2 Nm) was comparable to that of the standard constructs (25±4.6 Nm, p=0.54), as shown in FIG. 26B. Torsion induced spiral fractures at the plate end in all constructs. In bending, the strength of the dynamic constructs (38±3 Nm) was comparable to that of the standard constructs (31.3±3.2 Nm, p=0.06), as shown in FIG. 26C. All constructs failed by transverse fracture of the osteoporotic diaphysis adjacent to the outermost screw hole.

Discussion: Results of this biomechanical study were shown to support the hypothesis of the present inventors that dynamic plates symmetrically enhance interfragmentary motion and provide controlled axial dynamization while retaining strength comparable to standard locking plate constructs.

The finding that dynamic plates have a 77% lower axial stiffness than standard plates falls within the 74-88% range of axial stiffness reduction reported for DLS and FCL screws (see Bottlang M, Feist F. Biomechanics of far cortical locking *J Orthop Trauma* 2011; 25 Suppl 1:S21-8; Dobele S, Gardner M, Schroter S, Hontzsch D, Stockle U, Freude T. DLS 5.0—The Biomechanical Effects of Dynamic Locking Screws. *PLoS One* 2014; 9-4:e91933; and Doornink J, Fitzpatrick D C, Madey S M, Bottlang M. Far cortical locking enables flexible fixation with periarticular locking plates. *J Orthop Trauma* 2011; 25 Suppl 1:529-34). However, unlike with DLS and FCL screws, stiffness reduction was achieved within the plate by elastic suspension of screw holes, thereby retaining axial dynamization even when short screws are required for plate fixation in small diameter bones.

Driven by the growing awareness that axial dynamization is imperative for promotion of secondary bone healing, several alternative strategies have been recommended to mitigate the inherently high stiffness of locking plate constructs. These include the use of more flexible plates made of titanium rather than stainless steel, and increasing the plate span by bridging the fracture zone with a long segment of empty screw holes. Both of these strategies increase the amount of plate flexion in response to a given load, which in turn will increase motion at the far cortex, but not at the near cortex. The resulting asymmetric dynamization has been confirmed in the present biomechanical study, demonstrating that loading of standard constructs as high as 1,000 N will induce less than 0.2 mm axial dynamization at the near cortex, which is not sufficient to promote callus formation.

This biomechanical study also investigated the strength of dynamic constructs relative to standard constructs in both non-osteoporotic and osteoporotic bone since fixation strength and failure modes are highly affected by bone quality. Testing to failure in either bone quality under compression, torsion, and bending demonstrated that the dynamic constructs were at least as strong or stronger than the standard constructs. In non-osteoporotic specimens, the dynamic constructs had a 21% greater torsional strength than the standard constructs. This may be attributed to the mild staggering of screw holes in the dynamic plates, which imparts multi-planar stability under torsion. Conversely, the standard plates had a standard linear hole pattern centered along the plate midline, which allowed greater toggle of the elevated plate around its single plate of fixation. This resulted in fatigue fracture of screw shafts between the plate and bone due to repetitive screw shaft bending. This failure mode correlated with prior studies in which locking plates were applied to synthetic femurs at 1 mm elevation and failed in torsion as a result of screw breakage (see Bottlang M, Doornink J, Fitzpatrick D C, Madey S M. Far cortical locking can reduce stiffness of locked plating constructs while retaining construct strength. *J Bone Joint Surg Am* 2009; 91-8:1985-94; and Stoffel K, Booth G, Rohrl S M, Kuster M. A comparison of conventional versus locking plates in intraarticular calcaneus fractures: a biomechanical study in human cadavers. *Clin Biomech (Bristol, Avon)* 2007; 22-1:100-5). In osteoporotic specimens, the dynamic constructs also exhibited a 25% greater bending strength than the standard constructs. Both constructs failed by transverse fracture at the plate end. The superior bending strength of the dynamic constructs relative to the standard constructs appears to be attributable to elastic suspension of locking holes within the plate that improves load distribution and reduces stress concentrations and subsequent fracture at the plate end.

The dynamic plate design achieved axial dynamization by embedding individual sliding elements with locking holes into a silicone elastomer envelope that elastically suspends the locking hole within the plate and that prevents metal-on-metal contact between the sliding element and the plate. While the use of silicone elastomer is believed novel for osteosynthesis implants, long-term implantable silicone has been used clinically for a range of permanent implants, such as finger joints. Unlike silicone gel, the silicone elastomer used in finger joints and in the dynamic plates described herein is highly biocompatible and bioinert. With broad precedence and long clinical history, silicone elastomer enables a novel strategy to integrate classic fracture healing prerequisites into modern locking plates, namely controlled axial dynamization to promote secondary bone healing.

In conclusion, this biomechanical study demonstrated that dynamic locking plates symmetrically enhance interfragmentary motion, deliver controlled axial dynamization, and are at least comparable in strength to standard locking plate constructs. Since dynamic locking plates can be applied with standard locking screws, they can provide a more scalable alternative to DLS and FCL screws for dynamization of locking plate constructs.

It will be appreciated by those skilled in the art that changes could be made to the embodiments described above without departing from the broad inventive concept thereof. Specifically, the disclosed invention may be practiced for fixation of a bone plate to one side of a fracture only, whereby the corresponding side of a fractured bone may be applied to the one plate by alternative means for flexible or rigid fixation. It is understood, therefore, that this disclosure is not limited to the particular embodiments disclosed, but it is intended to cover modifications within the spirit and scope of the present disclosure as defined by the appended claims.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any combinations, adaptations, or variations of the embodiments discussed herein. Therefore, it is manifestly intended that embodiments be limited only by the claims and the equivalents thereof.

What is claimed is:

1. A device, comprising:
    a bone plate having an upper surface and a bone-facing surface, the bone plate comprising one or more openings extending through the bone plate from the upper surface to the bone-facing surface;
    one or more sliding elements, each sliding element including a fastener receiving hole, wherein the one or more openings at least partially surround a periphery of one of the receiving holes, and wherein the one or more openings are at least partially filled with an elastomer to support elastic suspension of the one or more sliding elements in the bone plate, thereby enabling relative displacement between the one or more sliding elements and the bone plate;
    at least one sensor operable to assess a dynamic parameter of one of the one or more sliding elements within the bone plate;
    a receiver element located external to the bone plate; and
    a transmission element operably coupled to the sensor, the transmission element configured to communicate with the receiver element.

2. The device of claim 1, wherein the sensor is operable to track a relative position of the sliding element relative to the bone plate.

3. The device of claim 1, wherein the sensor is operable to measure displacement of the sliding element relative to the bone plate.

4. The device of claim 1, wherein the sensor is operable to measure pressure within the elastomer that is suspending the sliding element in the bone plate.

5. The device of claim 4, wherein the sensor is positioned at least partially within the elastomer.

6. The device of claim 1, wherein the sensor is operable to measure pressure applied to the bone plate by the elastomer that is suspending the sliding element in the bone plate.

7. The device of claim 1, wherein the sensor is self-powered.

8. The device of claim 1, wherein the sensor is powered by an external power source.

9. A bone plate, comprising:
    a plate body having an upper surface and a bone-facing surface;
    a plurality of openings extending through the plate body from the upper surface to the bone-facing surface;
    one or more sliding elements each including a fastener receiving hole, each of the one or more sliding elements positioned within a different one of the openings such that the opening at least partially surrounds a periphery of the receiving hole;
    an elastomer layer at least partially surrounding each of the one or more sliding elements, thereby enabling relative displacement of the sliding element within the plate body;
    one or more sensors operable to assess a dynamic parameter of the one or more sliding elements within the plate body;
    a receiver element located external to the bone plate; and
    a transmission element operably coupled to the sensor, the transmission element configured to communicate with the receiver element.

10. The bone plate of claim 9, wherein each receiving hole is a threaded receiving hole.

11. The bone plate of claim 10, wherein each receiving hole is cylindrical.

12. The bone plate of claim 9, wherein the elastomer layer has a modulus of elasticity in the range of 0.1-50 MPa.

13. The bone plate of claim 9, wherein the elastomer layer is silicone.

14. The bone plate of claim 9, wherein the one or more sensors are operable to measure displacement, pressure, or load to capture a presence or magnitude of load transfer between the sensor and the plate body as a means for estimating the progression of fracture healing.

15. The bone plate of claim 9, wherein at least one elastomer layer includes an energy generation element to supply transient power to the one or more sensors.

16. The bone plate of claim 9, wherein the one or more sensors are powered by an external power source.

17. The bone plate of claim 9, further comprising one or more accelerometers to determine acceleration of the plate body or one or more of the sliding elements.

18. The bone plate of claim 17, comprising a first accelerometer operably coupled to the plate body and a second accelerometer operably coupled to one of the sliding elements.

19. The bone plate of claim 18, wherein the first and second accelerometers provide feedback to determine a relative acceleration of the sliding element with respect to the plate body.

20. A device, comprising:
a bone plate having an upper surface and a bone-facing surface, the bone plate comprising one or more openings extending through the bone plate from the upper surface to the bone-facing surface;
one or more sliding elements, each sliding element including a fastener receiving hole, wherein the one or more openings at least partially surround a periphery of one of the receiving holes, and wherein the one or more openings are at least partially filled with an elastomer to support elastic suspension of the one or more sliding elements in the bone plate, thereby enabling relative displacement between the one or more sliding elements and the bone plate;
at least one sensor operable to measure at least one of displacement, pressure, or load to capture a presence or magnitude of load transfer between the sensor and the bone plate and to estimate the progression of fracture healing;
a receiver element located external to the bone plate; and
a transmission element operably coupled to the sensor, the transmission element configured to communicate with the receiver element.

* * * * *